(12) United States Patent
Derosa et al.

(10) Patent No.: US 11,814,625 B2
(45) Date of Patent: Nov. 14, 2023

(54) APTAMERS AS A THERAPEUTIC TOOL TO PREVENT PROTEIN AGGREGATION IN NEURODEGENERATIVE DISEASE

(71) Applicant: Carleton University, Ottawa (CA)

(72) Inventors: Maria Cynthia Derosa, Ottawa (CA); Matthew Richard Holahan, Ottawa (CA); Erin Marie McConnell, Orleans (CA); Katelyn Victoria Ventura, Stittsville (CA); Joshua Parker Callahan, Ottawa (CA); Vernon Harold Daniel Hunt, Ottawa (CA)

(73) Assignee: Carleton University, Ottawa (CA)

( * ) Notice: Subject to any disclaimer, the term of this patent is extended or adjusted under 35 U.S.C. 154(b) by 480 days.

(21) Appl. No.: 16/758,090

(22) PCT Filed: Oct. 22, 2018

(86) PCT No.: PCT/CA2018/051335
§ 371 (c)(1),
(2) Date: Apr. 22, 2020

(87) PCT Pub. No.: WO2019/079887
PCT Pub. Date: May 2, 2019

(65) Prior Publication Data
US 2020/0325476 A1     Oct. 15, 2020

Related U.S. Application Data

(60) Provisional application No. 62/575,813, filed on Oct. 23, 2017.

(51) Int. Cl.
*C12N 15/115*    (2010.01)
*A61K 9/127*    (2006.01)
*G01N 33/68*    (2006.01)

(52) U.S. Cl.
CPC ............ *C12N 15/115* (2013.01); *A61K 9/127* (2013.01); *G01N 33/6896* (2013.01)

(58) Field of Classification Search
CPC ........ A61K 9/00; A61K 9/127; A61K 9/0085; A61K 47/00; A61K 47/549; A61K 47/6911; C12N 15/115; C12N 2310/16; G01N 33/6896; G01N 2800/2835; A61P 25/28; A61P 25/16; C40B 30/04
USPC .......... 424/1.11, 1.49, 1.64, 1.69, 1.73, 1.81, 424/1.85, 1.89, 9.1, 9.2, 9.6; 530/300; 514/1, 1.1
See application file for complete search history.

(56) References Cited

U.S. PATENT DOCUMENTS 9,238,816 B2 * 1/2016 Ikebukuro ............ C12N 15/115

FOREIGN PATENT DOCUMENTS

EP           2677032 A1    12/2013
WO    WO-2014/064257 A1    5/2014

OTHER PUBLICATIONS

Tsukakoshi et al., Biotechnology Letter, vol. 32, pp. 643-648 (Year: 2010).*
Angelova et al., "Alpha-synuclein and beta-amyloid—different targets, same players: calcium, free radicals and mitochondria in the mechanism of neurodegeneration," Biochem Biophys Res Commun. 483(4):1110-1115 (2017).
Chaudhary et al., "Inhibition of Aggregation of Mutant Huntingtin by Nucleic Acid Aptamers In Vitro and in a Yeast Model of Huntington's Disease," Mol Ther. 23(12):1912-26 (2015).
Tuerk et al., "Systematic Evolution of Ligands by Exponential Enrichment: RNA Ligands to Bacteriophage T4 DNA Polymerase," Science. 249(4968): 505-510 (1990).
Ellington et al., "Selection in vitro of single-stranded DNA molecules that fold into specific ligand-binding structures," Nature. 355(6363):850-2 (1992).
Tolle et al., "Dressed for success—applying chemistry to modulate aptamer functionality," Chem Sci. 40(60): 60 (2013).
Giasson et al., "Neuronal alpha-synucleinopathy with severe movement disorder in mice expressing A53T human alpha-synuclein," Neuron. 34(4):521-33 (2016).
Hickey et al., "Available and emerging treatments for Parkinson's disease: a review," Drug Des Devel Ther. 5:241-54 (2011).
Hoinka et al., "Large scale analysis of the mutational landscape in HT-SELEX improves aptamer discovery. Nucleic Acids Res," 43(12):5699-707 (2015).
Hoinka et al., "AptaCluster—A Method to Cluster HT-SELEX Aptamer Pools and Lessons from its Application," Res Comput Mol Biol. 8394:115-128 (2014).
International Search Report and Written Opinion for International Application No. PCT/CA2018/051335, dated Jan. 25, 2019 (14 pages).
Jesko et al., "Treatments and compositions targeting a-synuclein: a patent review (2010-2016)," Expert Opin Ther Pat. 27(4):427-438 (2017).
McKeague et al., "Analysis of In Vitro Aptamer Selection Parameters," J Mol Evol. 81(5-6):150-61 (2015).
Müller et al., "Anticoagulant characteristics of HD1-22, a bivalent aptamer that specifically inhibits thrombin and prothrombinase," J Thromb Haemost. 6(12):2105-12 (2008).

(Continued)

*Primary Examiner* — D. L. Jones
(74) *Attorney, Agent, or Firm* — Clark & Elbing LLP

(57) ABSTRACT

The present disclosure relates generally to the selection of DNA aptamers that prevent aggregation, or fibrilization of alpha-synuclein protein. The aptamers described herein are of use as a therapeutic tool to prevent protein aggregation in neurodegenerative disease.

18 Claims, 18 Drawing Sheets
(2 of 18 Drawing Sheet(s) Filed in Color)
Specification includes a Sequence Listing.

(56) References Cited

OTHER PUBLICATIONS

Rhie et al., "Characterization of 2'-fluoro-RNA aptamers that bind preferentially to disease-associated conformations of prion protein and inhibit conversion," J Biol Chem. 278(41):39697-705 (2003).
Rosborough et al., "c-Synuclein and Parkinsonism: Updates and Future Perspectives," Curr Neurol Neurosci Rep. 17(4):31 (2017).
Ruigrok et al., "Alternative affinity tools: more attractive than antibodies," Biochem J. 436(1):1-13 (2011).
Rusconi et al., "RNA aptamers as reversible antagonists of coagulation factor IXa," Nature. 419(6902):90-4 (2002).
Singh et., "α-Synuclein aggregation modulation: an emerging approach for the treatment of Parkinson's disease," Future Med Chem. 9(10):1039-1053 (2017).
Sun, "Aptasensors for the selective detection of alpha-synuclein oligomer by colorimetry, surface plasmon resonance and eletrochemical impedance spectroscopy," Sensors and Actuators B: Chemical. 245(2):87-94 (2017).
Takahashi et al., "RNA aptamers selected against amyloid beta-peptide (Abeta) inhibit the aggregation of Abeta," Mol Biosyst. 5(9):986-91 (2009).
Tsukakoshi et al., "Selection of DNA aptamers that recognize a-synuclein oligomers using a competitive screening method," Anal Chem. 84(13):5542-7 (2012).
Tsukakoshi et al., "Screening of DNA aptamer which binds to a-synuclein," Biotechnology Letters. 32(5): 643-648 (2010).
Wong et al., "α-synuclein toxicity in neurodegeneration: mechanism and therapeutic strategies," Nat Med. 23(2):1-13 (2017).
Zheng et al., "Novel DNA Aptamers for Parkinson's Disease Treatment Inhibit a-Synuclein Aggregation and Facilitate its Degradation," Mol Ther Nucleic Acids. (11): 228-242 (2018).
Office Action issued in Canadian Patent Application No. 3,079,909, dated Aug. 23, 2023 (5 pages).

* cited by examiner

S1:

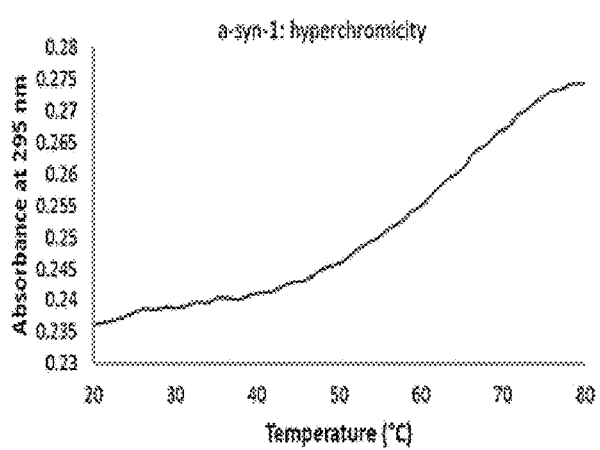 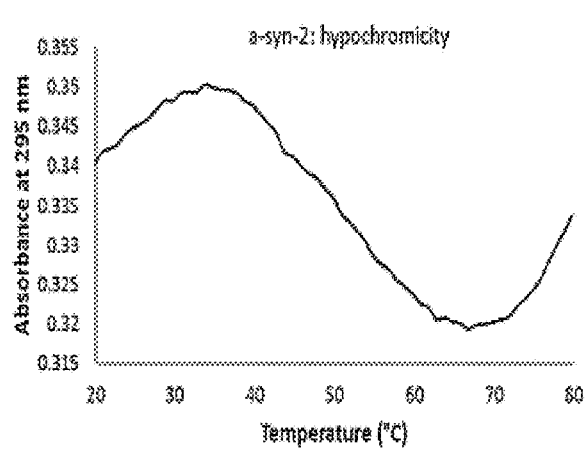
FIG. 10A
FIG. 10B

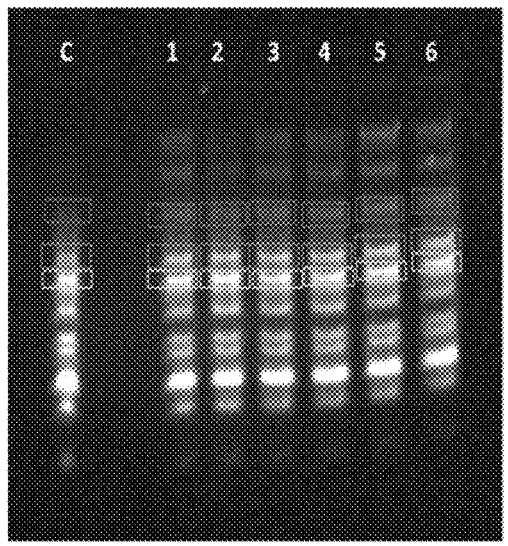
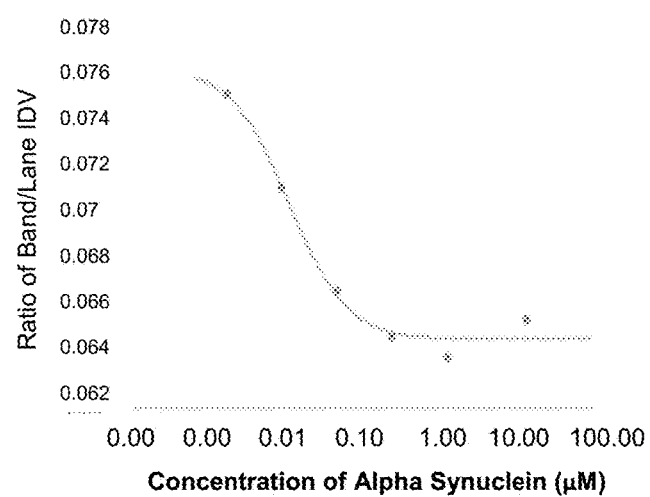
FIG. 15A
FIG. 15B
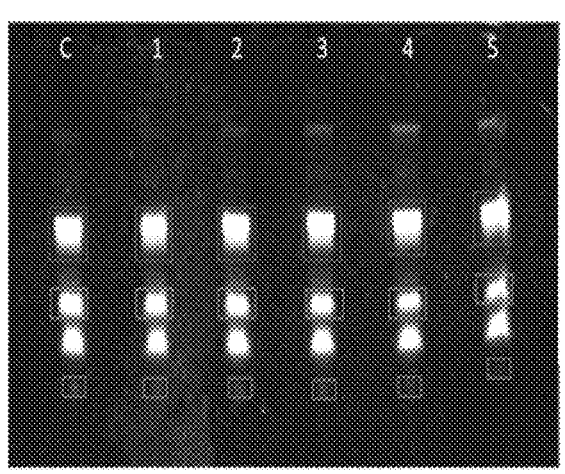
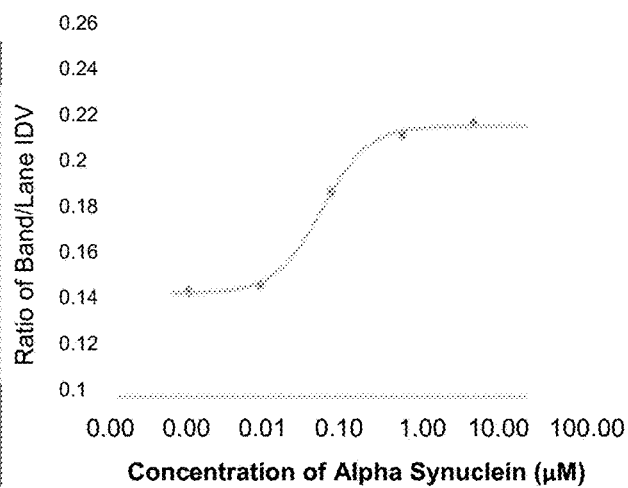
FIG. 16A
FIG. 16B

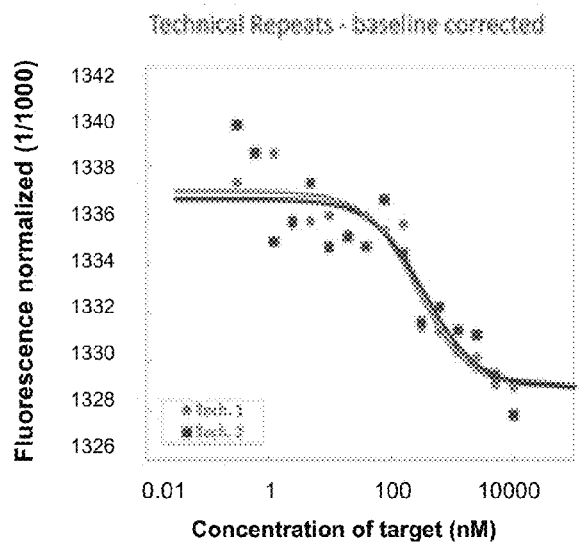
FIG. 19A
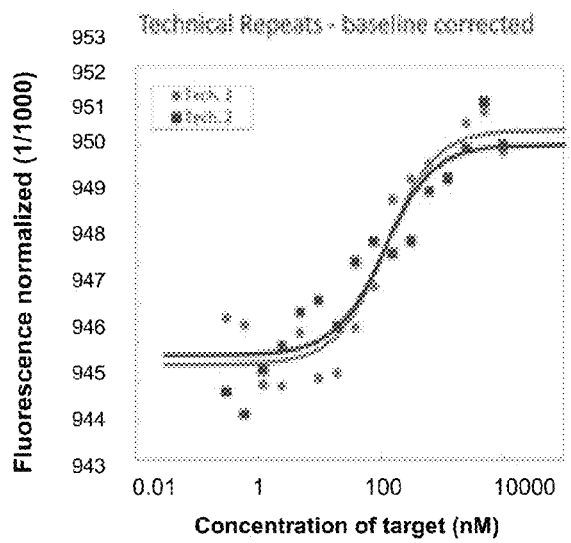
FIG. 19B
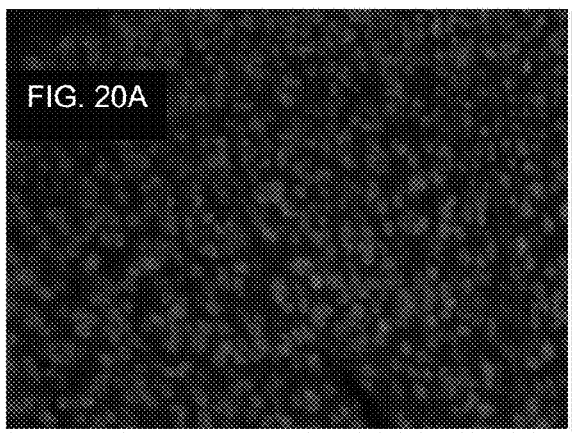

APTAMERS AS A THERAPEUTIC TOOL TO PREVENT PROTEIN AGGREGATION IN NEURODEGENERATIVE DISEASE

SEQUENCE LISTING

The instant application contains a Sequence Listing which has been submitted electronically in ASCII format and is hereby incorporated by reference in its entirety. Said ASCII copy, created on Apr. 24, 2020, is named 51012_031001_Sequence_Listing_04.24.2020_ST25 and is 7,527 bytes in size.

FIELD

The present disclosure relates generally to the selection of DNA aptamers that prevent aggregation, or fibrilization of alpha-synuclein protein.

BACKGROUND

Parkinson's disease is a multifactorial neurodegenerative disease, which manifests clinically with severe, progressive motor symptoms.[1] The cause of sporadic Parkinson's disease is unknown; however, the misfolding and aggregation of alpha-synuclein protein has been shown to be a pathological hallmark of the disease.[1,2] Additionally, the aggregation of alpha-synuclein has been observed in dementia with Lewy bodies and multiple system atrophy so may be a common mechanism in the etiology of a variety of neurodegenerative diseases.[3]

Alpha-synuclein, which is encoded by the SNCA gene, is a relatively small protein (~14.6 kDa) made up of 140 amino acids.[3-5]

Evidence suggests that the function of alpha-synuclein is to bind lipids at the presynaptic terminal and regulate the release of synaptic vesicles, as well as regulate amyloid-β and tau protein fibrilization.[5] The role of alpha-synuclein accumulation in synaptic dysfunction, mitochondrial impairment, endoplasmic reticulum dysfunction, autophagy-lysosomal pathway dysfunction, and nuclear dysfunction was recently reviewed.[5]

A common therapeutic strategy for synucleinopathies is to regulate or control alpha-synuclein aggregation by either preventing aggregation, or inducing deaggregation.[6,7]

SUMMARY

In one aspect, there is described an aptamer that binds to alpha-synuclein protein, comprising:
  a) a nucleic acid comprising or consisting of any one of α-syn-1(SEQ ID NO: 1), α-syn-2(SEQ ID NO: 2), α-syn-3(SEQ ID NO: 3), α-syn-4(SEQ ID NO: 4), or α-syn-5(SEQ ID NO: 5);
  b) a nucleic acid having at least 70% sequence identity to the nucleic acid sequence of a);
  c) a nucleic acid that hybridizes with the complementary strand of the nucleic acid of a);
  d) a nucleic acid that differs from a) by one or more nucleotides that are substituted, deleted, and/or inserted; or
  e) a derivative of a), b), c), or d).

In one example, wherein in step (b) said nucleic acid has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identify.

In one example, wherein in step (c) said nucleic acid hybridizes with the complementary strand of the nucleic acid of a) under conditions of high stringency.

In one aspect, there is described a method for producing a nucleic acid aptamer, comprising:
  (a) a complex formation step of mixing a single-stranded nucleic acid library with alpha-synuclein protein monomers in a solution to form a complex of a single-stranded nucleic acid and the alpha-synuclein protein monomers,
  (b) an aggregation step to promote aggregation of alpha-synuclein monomers to larger order aggregates such as fibrils,
  (c) a recovery step of recovering the complex from the solution;
  (d) an amplification step of recovering the single-stranded nucleic acid from the complex and then amplifying the single-stranded nucleic acid by a nucleic acid amplification method; and
  (e) a single-stranded nucleic acid preparation step of converting the double-stranded nucleic acids obtained in the amplification step into single strands and then forming an intramolecular conformation.

In one example, said recovery step comprises a size selection step.

In one example, said recovery step comprises an ultracentrifugation step.

In one aspect, there is described a liposome comprising, one or more lipids, and at least one aptamer of any one of claims 1 to 3.

In one example, further comprising a targeting moiety.

In one example, wherein said targeting moiety is a transferrin receptor aptamer.

In one aspect, there is described a method of treating a subject having, or suspected of having, a neurodegenerative disease, comprising: administering at least one aptamer of any one of claims 1 to 3.

In one aspect, there is described a method of treating a subject having, or suspected of having, a neurodegenerative disease, comprising: administering a pharmaceutical composition comprising at least one aptamer of any one of claims 1 to 3, and a pharmaceutically acceptable carrier.

In one example, wherein said neurodegenerative disease is Parkinson's disease (PD), dementia with Lewy bodies (DLB), or multiple system atrophy (MSA).

In one example, wherein said subject is a human.

In one aspect, there is described a method of treating a subject having, or suspected of having, a neurodegenerative disease, comprising: administering a liposome comprising at least one aptamer of any one of claims 1 to 3, and optionally comprising a pharmaceutically acceptable carrier.

In one example, wherein said liposome further comprising a targeting moiety.

In one example, wherein said targeting moiety is a transferrin receptor aptamer.

In one example, wherein said neurodegenerative disease is Parkinson's disease (PD), dementia with Lewy bodies (DLB), or multiple system atrophy (MSA).

In one example, wherein said subject is a human.

In one aspect, there is described a use of an aptamer of any one of claims 1 to 3, for treating a subject having, or suspected of having, a neurodegenerative disease.

In one aspect, there is described a use of an aptamer of any one of claims 1 to 3, in the manufacture of a medicament for treating a subject having, or suspected of having, a neurodegenerative disease.

In one aspect, there is described a use of a pharmaceutical composition comprising at least one aptamer of any one of claims 1 to 3, and a pharmaceutically acceptable carrier, for treating a subject having, or suspected of having, a neurodegenerative disease.

In one aspect, there is described a use of a pharmaceutical composition comprising at least one aptamer of any one of claims 1 to 3, and a pharmaceutically acceptable carrier, in the manufacture of a medicament for treating a subject having, or suspected of having, a neurodegenerative disease.

In one example, wherein said neurodegenerative disease is Parkinson's disease (PD), dementia with Lewy bodies (DL), or multiple system atrophy (MSA).

In one example, wherein said subject is a human.

In one aspect, there is described a use of a liposome comprising at least aptamer of any one of claims 1 to 3, and optionally a pharmaceutically acceptable carrier, for treating a subject having, or suspected of having, a neurodegenerative disease.

In one aspect, there is described a use of a liposome comprising at least one aptamer of any one of claims 1 to 3, and optionally a pharmaceutically acceptable carrier, in the manufacture of a medicament for treating a subject having, or suspected of having, a neurodegenerative disease.

In one example, wherein said liposome further comprising a targeting moiety.

In one example, wherein said targeting moiety is a transferrin receptor aptamer.

In one example, wherein said neurodegenerative disease is Parkinson's disease (PD), dementia with Lewy bodies (DL), or multiple system atrophy (MSA).

In one example, wherein said subject is a human.

In one aspect, there is described a method for detecting alpha-synuclein polypeptide in a biological sample, comprising: contacting said sample with an aptamer of any one of claims 1 to 3, said aptamer comprising a detectable label, and determining whether an increase in fluorescence occurs, wherein an increase in fluorescence is indicative of the presence of alpha-synuclein polypeptide in the sample.

In one aspect, there is described a kit comprising one or more aptamers that binds to alpha-synuclein protein, comprising:
  a) a nucleic acid comprising or consisting of any one of α-syn-1(SEQ ID NO: 1), α-syn-2(SEQ ID NO: 2), α-syn-3(SEQ ID NO: 3), α-syn-4(SEQ ID NO: 4), or α-syn-5(SEQ ID NO: 5);
  b) a nucleic acid having at least 70% sequence identity to the nucleic acid sequence of a);
  c) a nucleic acid that hybridizes with the complementary strand of the nucleic acid of a);
  d) a nucleic acid that differs from a) by one or more nucleotides that are substituted, deleted, and/or inserted; or
  e) a derivative of a), b), c), or d), and optionally instructions.

In one example, comprising one or more aptamers selected from SEQ ID NO: 1, SEQ ID NO: 2, SEQ ID NO: 3, SEQ ID NO: 4, SEQ ID NO: 5.

In one example, further comprising a detectable label.

In one example, further comprising a targeting moiety.

In one example, further comprising a transferrin receptor aptamer.

In one example, further comprising a neutral lipid, an anionic lipid, a cationic lipid, or a Zwitterionic lipid.

BRIEF DESCRIPTION OF THE FIGURES

Embodiments of the present disclosure will now be described, by way of example only, with reference to the attached Figures.

The application file contains at least one drawing executed in color. Copies of this patent or patent application with color drawings will be provided by the Office upon request and payment of the necessary fee.

FIGS. 10A-10B: Thermal denaturation (tracked by UV-Vis spectroscopy) was used to evaluate the M5-15 aptamer and aptamer candidates for the presence of G-quadruplex secondary structure. The absorbance of the aptamer in the presence of 140 mM NaCl at 295 nm was monitored over the temperature gradient of 20° C.-80° C. Representative traces are shown for α-syn-1 (FIG. 10A) and α-syn-2 (FIG. 10B). M5-15 showed hypochromicity at 295 nm (data not shown) and the remaining aptamer candidates showed hyperchromicity at 295 nm (data not shown).

FIGS. 15A-15B: The DNA footprint (left) (FIG. 15A) produced by the interaction of DNase I with the α-syn-1 aptamer-alpha synuclein monomer binding complex is shown. Lanes contained 10 μM DNA and alpha synuclein at the following concentrations: 0 μM (C), 15 μM (1), 1.5 μM (2), 0.3 μM (3), 0.06 μM (4), 0.012 μM (5) and 0.0024 μM (6). The changes in the relative integrated density value (IDV) of three bands (highlighted by top, middle, and bottom boxes) were used to estimate the apparent KD of the aptamer-target interaction. (FIG. 15B) A sample binding isotherm, generated from the middle boxed data, is shown (right).

FIGS. 16A-16B: The DNA footprint (left) (FIG. 16A) produced by the interaction of DNase I with the positive control M5-15 aptamer-alpha synuclein monomer binding complex is shown. Lanes contained 10 μM DNA and alpha synuclein at the following concentrations: 0 μM (C), 17.5 μM (1), 1.75 μM (2), 0.175 μM (3), 0.0175 μM (4), and 0.00175 μM (5). The changes in the relative integrated density value (IDV) of three bands (top, middle, and bottom boxes) were used to estimate the apparent KD of the aptamer-target interaction. (FIG. 16B) A sample binding isotherm, generated from the middle boxed data, is shown (right).

FIGS. 19A-19B depicts binding isotherms provided from 2bind for the (FIG. 19A) α-syn-2, (FIG. 19B) α-syn-3, The dissociation constant of α-syn-2 and α-syn-3 were calculated to be 285.5 nM±37.9 nM, 94.2 nM±2.8 nM, respectively.

FIGS. 20A-20B depicts Slices from motor cortex (FIG. 20A) of A53T alpha-synuclein transgenic line M83 mouse model (12 months old) vs. age matched wild type mouse (FIG. 20B) both stained with 5'-fluorescein modified asyn1.

DETAILED DESCRIPTION

Figure 1:
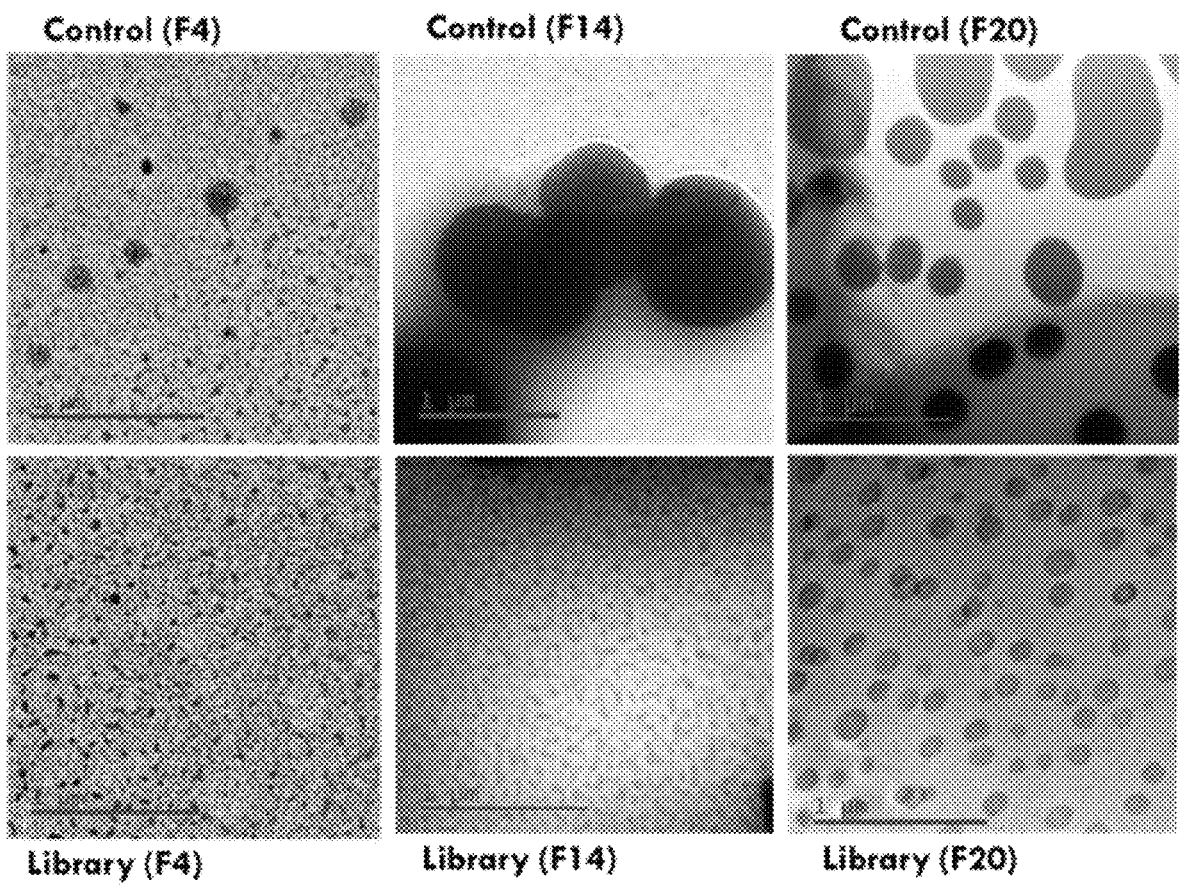
FIG. 1: Transmission electron microscopy was employed to monitor the aggregation of alpha-synuclein in the absence (control) and presence (library) of the DNA aptamer pool. Representative images from the second round of selection are shown. Fractions were collected after ultracentrifugation. Fraction 4 was expected to contain free monomer/free DNA. Fraction 14 was expected to contain monomer bound DNA, and Fraction 20 was chosen to represent DNA bound to larger aggregates.

In one aspect, there is described a Systematic Evolution of Ligands by EXponential enrichment (SELEX) method of producing one or more aptamers that binds to alpha-synuclein polypeptide.

In some examples, the aptamers bind to a monomeric form of alpha-synuclein polypeptide.

In some examples, the aptamers may be used to prevent or reduce polymerization of the monomeric form of alpha-synuclein polypeptide.

In some examples, the aptamers may be used to prevent or reduce fibrilization of alpha-synuclein polypeptide.

In one example, there is described the use of one or more aptamers that may be used for the treatment of a subject having or suspected of having a neurodegenerative disease. In a specific example, the neurodegenerative disease is Parkinson's disease (PD), dementia with Lewy bodies (DL), or multiple system atrophy (MSA).

Alpha-Synuclein

The term "alpha-synuclein", "α-synuclein" or "α-syn" as used herein refers to a protein which is encoded by the SNCA gene. A nucleotide sequence of the alpha-synuclein gene may be obtained from known databases, such as GenBank of NCBI, etc.

The human alpha-synuclein polypeptide is made up of 140 amino acid (~14.6 kDa). While not wishing to be bound by theory, evidence suggests that the function of alpha-synuclein polypeptide is to bind lipids at the presynaptic terminal and regulate the release of synaptic vesicles.

Misfolding, aggregation and fibrillation of alpha-synuclein polypeptide are implicated as factors in several neurodegenerative diseases.

The term "neurodegenerative disease" refers to a disease of the brain caused by progressive neuronal damage or loss. In some examples, the neurodegenerative disease is a disease associate with alpha-synuclein. In some examples, the neurodegenerative disease is Parkinson's disease (PD), dementia with Lewy bodies (DLB), or multiple system atrophy (MSA).

A therapeutic strategy for alpha-synuclein related disease is to regulate or control alpha-synuclein aggregation by either preventing aggregation, or inducing deaggregation.

As used herein, "alpha-synuclein related disease" or "Synuclein diseases" or "synucleinopathies" refers to diseases associated with the formation, deposition, accumulation, or persistence of α-synuclein fibrils. Such diseases include, but are not limited to Parkinson's disease, dementia with Lewy bodies, and multiple system atrophy In some example, the therapeutic strategy is inhibition of fibrillogenesis.

As used herein, "inhibition of fibrillogenesis" refers to the inhibition of formation, deposition, accumulation and/or persistence fibrils or alpha-synuclein fibril-like deposits.

In some example, the therapeutic strategy is disruption of fibrils or fibrillogenesis.

As used herein, "disruption of fibrils or fibrillogenesis" refers to the disruption of pre-formed alpha-synuclein fibrils. Such disruption by compounds provided herein may involve reduction or disassembly of alpha-synuclein fibrils as assessed by various methods such as Thioflavin T fluorometry, Congo red binding, circular dichroism spectra, thioflavin S and cell based assays.

In one example, one or more aptamers may be used to prevent or reduce alpha-synuclein polypeptide aggregation.

In one example, one or more aptamers may be used to treat a subject having, or suspected of having, a neurodegenerative disease.

Aptamers and Selective Evolution of Ligands by Exponential Enrichment (SELEX)

The term "aptamer" as used herein refers to single-stranded nucleic acid molecules with secondary structures that facilitate high-affinity binding to a target molecule.

As used herein, "nucleic acid molecules" or "nucleic acid sequence" are interchangeable with the term "polynucleotide(s)" and it generally refers to any polyribonucleotide or poly-deoxyribonucleotide, which may be unmodified RNA or DNA or modified RNA or DNA or any combination thereof. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells.

In some examples, one or more nucleotides are modified at the base, sugar or backbone to make the nucleic acid more stable or less likely to be cleared e.g. phosphorothioate backbone, pegylated backbone.

A "target" molecule may be any compound upon which a nucleic acid can interact in a desired manner. For example, a target molecule may be a polypeptide, peptide, nucleic acid, carbohydrate, lipid, polysaccharide, glycoprotein, hormone, receptor, antigen, antibody, virus, pathogen, toxic substance, substrate, metabolite, etc. A target also includes variations of a particular compound or molecule, such as, in the case of a polypeptide, for example, variations in amino acid sequence, disulfide bond formation, glycosylation, lipidation, acetylation, phosphorylation, or any other manipulation or modification, such as conjugation with a labeling component, which does not substantially alter the identity of the molecule.

In a specific example, the target is a polypeptide.

The term "polypeptide" refers to amino acid chains of any length, including full length sequences in which amino acid residues are linked by covalent peptide bonds. Polypeptides may be isolated natural products, or may be produced partially or wholly using recombinant or synthetic techniques. Thus, the term "polypeptide" may also refer to "protein".

The term "isolated" refers to sequences that are removed from their natural cellular or other naturally occurring biological environment or from the environment of the experiment. An isolated molecule may be obtained by any method or combination of methods including biochemical, recombinant, and synthetic techniques. The polypeptide sequences may be prepared by at least one purification step.

The term "purified" as used herein does not require absolute purity. Purified refers in various embodiments, for example, to at least about 80%, 85%, 90%, 95%, 98%, or 99% homogeneity of a polypeptide, for example, in a sample.

In one example, the polypeptide is alpha-synuclein.

In a more specific example, the alpha-synuclein is human alpha-synuclein polypeptide.

In a more specific example, the polypeptide is a monomeric form of alpha-synuclein.

Selective Evolution of Ligands by Exponential enrichment (SELEX) refers to a process that combines the selection of nucleic acids that interact with a target in a desirable manner (e.g., binding to a protein) with the amplification of those selected nucleic acids. Optional iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. In some embodiments of the SELEX process, aptamers that bind non-covalently to their targets are generated. In other embodiments of the SELEX process, aptamers that bind covalently to their targets are generated.

The SELEX target is as described above and herein with respect to "target".

In one example, the SELEX target comprises or consists of alpha-synuclein polypeptide. In one example, the SELEX target comprises or consists of alpha-synuclein polypeptide monomer.

Methods of SELEX are known. A generalized SELEX method may be described as follow.

1) A complex formation step in which a mixture of nucleic acids of differing sequence is prepared is contacted with a selected target under conditions favorable for binding between the target and members of the candidate mixture. Under these conditions, the interaction between the target and the nucleic acids of the candidate mixture can be considered as forming nucleic acid-target complexes between the target and those nucleic acids having the strongest affinity for the target.

2) The nucleic acids with the highest affinity for the target are partitioned from those nucleic acids with lesser affinity to the target. Because only a small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5 to 50%) are retained during partitioning.

3) Those nucleic acids selected during partitioning as having the relatively higher affinity to the target are then amplified to create a new candidate mixture that is enriched in nucleic acids having a relatively higher affinity for the target.

4) The partitioning and amplifying steps are repeated, and the newly formed candidate mixture contains fewer and fewer weakly binding sequences, and the average degree of affinity of the nucleic acids to the target will generally increase.

Accordingly, a SELEX process may yield a candidate mixture containing one or a small number of unique nucleic acids representing those nucleic acids sequences from the original candidate mixture which fold into a specific secondary and tertiary structure enabling the highest affinity interaction with the target molecule.

Identification of aptamers that bind to alpha-synuclein polypeptide.

As described herein, there is provided a SELEX method of producing a nucleic acid aptamer that binds to alpha-synuclein polypeptide. In a specific example, the aptamer binds to alpha-synuclein polypeptide monomer.

In one example, there is described a method for producing a nucleic acid aptamer, comprising:

(a) a complex formation step of mixing a single-stranded nucleic acid library with alpha-synuclein protein monomers in a solution to form a complex of a single-stranded nucleic acid and the alpha-synuclein protein monomers, (b) an aggregation step to promote aggregation of alpha-synuclein monomers to oligomers, from step (a), (c) a recovery step of recovering the complex from the solution;

(d) an amplification step of recovering the single-stranded nucleic acid from the complex and then amplifying the single-stranded nucleic acid by a nucleic acid amplification method; and (e) a single-stranded nucleic acid preparation step of converting the double-stranded nucleic acids obtained in the amplification step into single strands and then forming an intramolecular conformation.

In one example, the nucleic acid aptamer may be a natural nucleic acid such as a DNA, an RNA, or a combination thereof. Also, the nucleic acid may partially or wholly comprise a non-natural nucleotide or a non-natural nucleic acid.

In a specific example, the nucleic acid is a DNA. Thus, in one example the aptamer is a DNA aptamer.

The term "binds specifically" refers to high avidity and/or high affinity binding of an aptamer to a target, for example alpha-synuclein polypeptide monomer. Aptamers which bind specifically to a target of interest may be capable of binding other polypeptides at weak, yet detectable, level. Such weak binding, or background binding, is readily discernable from the specific aptamer binding to the compound or polypeptide of interest, e.g., by use of appropriate controls, as would be known to the worker skilled in the art.

In one example, to induce aggregation, the incubation reaction in round 1-3 is flash frozen, then lyophilized.

It will be appreciated that alternate and/or additional methods of aggregation may be used.

In some example, an MJFF protocol may be used, which involved preparing 5 mg/mL monomer in PBS and placing on an orbital shaker for 7 days at 37° C. (michaeljfox.org/files/accelerate/models/PFF%20Protocol%20for%20aSyn%20protein%20at%20Proteos.pdf), it may be carried out done chemically using SDS (combined with agitation: Giehm et al., J. Mol. Biol. 401:115-133, 201010.1016/j.jmb.2010.05.060.). It will be appreciated that, environmental factors that affect aggregation: low pH, certain metals and pesticides, polyanions, polycations and low concentrations of organic solvents cause a significant acceleration of alpha-synuclein fibrillation in the presence of high concentrations of polyethylene glycol. (PMID: 19519306).

In one example, the recovery step(s), step (e), may comprise or consist of a size selection step (for example based on molecular weight) to isolate aptamers bound to alpha-synuclein polypeptide monomers.

In one example, the recovery step(s) comprises or consists of an ultracentrifugation step to isolate aptamers bound to alpha-synuclein monomers.

In one example, the recover step comprises or consists of fractionation by ultracentrifugation.

In other example, fractionation may also consist or comprise of size exclusion chromatography, fractionation by size exclusion filtration.

It will be appreciated that alternate and/or additional method of recovery may be used. For example, capillary electrophoresis, In one example, to apply further selective pressure, a secondary incubation period is employed after one or more of the recovery steps.

In one example, to isolate the highest affinity aptamers from those which bound to the polypeptide monomer, nitrocellulose filtration was employed following the secondary incubation.

In one example, in which the target is alpha-synuclein polypeptide, the following aptamer were identified using the methods described herein (Table 1).

TABLE 1

| Aptamer | Sequence (5'→3') | SEQ ID NO: |
|---|---|---|
| a-syn-1 (1LBwAAjJ) | ATAGTCCCATCATTCATTGTAAGGAA ACGCTACGGGGTGGGTACGGCAAG ATATTAGCAAGTGTCA | SEQ ID NO: 1 |
| a-syn-2 (1LBiGJFJC) | ATAGTCCCATCATTCATTGTATGGTA CGGCGCGGTGGCGGGTGCGGGGA GATATTAGCAAGTGTCA | SEQ ID NO: 2 |
| a-syn-3 (GdJUhe) | ATAGTCCCATCATTCATTGTATGAGA TGGGGTGGTGACGTCAGCATGGAG ATATTAGCAAGTGTCA | SEQ ID NO: 3 |

TABLE 1-continued

| Aptamer | Sequence (5'→3') | SEQ ID NO: |
| --- | --- | --- |
| a-syn-4 (LTMul1) | ATAGTCCCATCATTCATTGAACGGAA TGGCGCGGTGACCGGATAGTGTAGA TATTAGCAAGTGTCA | SEQ ID NO: 4 |
| a-syn-5 (JueRc) | ATAGTCCCATCATTCATTGTATGATA CAGTGAGGTGGCAGATGCATGCAGA TATTAGCAAGTGTCA | SEQ ID NO: 5 |

Thus, in one example, an alpha-synuclein aptamer comprises or consists of the nucleic acid sequence selected from one or more of the aptamers of SEQ ID NO: 1, SEQ ID NO: 2, SEQ ID NO: 3, SEQ ID NO: 4, or SEQ ID NO: 5.

In some examples, there is described an aptamer that binds to alpha-synuclein protein, comprising:
  a) a nucleic acid comprising or consisting of any one of α-syn-1(SEQ ID NO: 1), α-syn-2(SEQ ID NO: 2), α-syn-3(SEQ ID NO: 3), α-syn-4(SEQ ID NO: 4), or α-syn-5(SEQ ID NO: 5);
  b) a nucleic acid having at least 70% sequence identity to the nucleic acid sequence of a);
  c) a nucleic acid that hybridizes with the complementary strand of the nucleic acid of a);
  d) a nucleic acid that differs from a) by one or more nucleotides that are substituted, deleted, and/or inserted; or
  e) a derivative of a), b), c), or d).

In some examples, the alpha-synuclein aptamer is a truncated aptamer comprising or consisting of the nucleic acid sequence selected from one or more of the aptamers SEQ ID NO: 1, SEQ ID NO: 2, SEQ ID NO: 3, SEQ ID NO: 4, or SEQ ID NO: 5, having less than 66 bases. In some examples, the truncated aptamer comprises or consists of 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 bases, selected from one or more of the aptamers of SEQ ID NO: 1, SEQ ID NO: 2, SEQ ID NO: 3, SEQ ID NO: 4, or SEQ ID NO: 5.

In another example, the alpha-synuclein aptamer is a "fragment" of one or more of the aptamers SEQ ID NO: 1, SEQ ID NO: 2, SEQ ID NO: 3, SEQ ID NO: 4, or SEQ ID NO: 5.

A "fragment" of the aptamer sequence may comprise a subsequence that binds to the same target as the full length sequence.

In one example, an alpha-synuclein aptamer is a derivative of one or more of the aptamers SEQ ID NO: 1, SEQ ID NO: 2, SEQ ID NO: 3, SEQ ID NO: 4, or SEQ ID NO: 5.

The term "derivative" as used herein refers to an aptamer which has a chemical structure which does not occur in natural DNA or RNA.

The nucleotide sequences of aptamers identified using the methods described herein, can be modified. In some examples, the aptamer contains one or more chemical modifications. The modifications may be various distinct modifications. In some embodiments, the regions may contain one, two, or more (optionally different) nucleoside or nucleotide modifications.

In some examples, there is provided an aptamer which is derived from an aptamer comprising or consisting of one or more of SEQ ID NO: 1, SEQ ID NO: 2, SEQ ID NO: 3, SEQ ID NO: 4, or SEQ ID NO: 5, such that in one of the sequences one or nucleotides are substituted, removed (deleted), added within the sequence (inserted) and/or added at the 5' end and/or 3' end, wherein such an aptamer binds to alpha-synuclein polypeptide, more preferably alpha-synuclein polypeptide monomer.

The term "sequence identity" as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

In some example, the aptamer has a nucleotide sequence that is at least 70% identical to the nucleotide sequence of one or more of SEQ ID NO: 1, SEQ ID NO: 2, SEQ ID NO: 3, SEQ ID NO: 4, or SEQ ID NO: 5, wherein such an aptamer binds to alpha-synuclein. In one example, the sequence identity is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some examples, there is provided an aptamer that hybridizes with a nucleotide sequence of one or more of SEQ ID NO: 1, SEQ ID NO: 2, SEQ ID NO: 3, SEQ ID NO: 4, or SEQ ID NO: 5, or to their complementary strand, under stringency conditions described below.

As used herein, the term "hybridizes under low stringency, medium stringency, or high stringency" describes conditions for hybridization and washing. Aqueous and non-aqueous methods can be used.

Therapeutic Uses

The alpha-synuclein aptamers described herein may be useful for the treatment of a subject having, or suspect of having, a neurodegenerative disease.

The term "subject" or "patient" as used herein, refers to any mammal or non-mammal that would benefit from determining the benefit from treatment, diagnosis, therapeutic monitoring and/or prognosis. In certain examples a subject or patient includes, but is not limited to, humans, farm animals, companion animals (such as cats, dogs and horses), primates and rodent (such as mice and rats). In a specific embodiment, the subject is a human. In an additional specific embodiment, the subject is female. In another example the subject is male.

The term "treat" or "treatment" as used herein, refers to clinical intervention in an attempt to alter the course of the subject or cell being treated. In non-limiting examples, treatment includes preventing or delaying recurrence of disease, alleviation of symptoms, diminishment of any direct or indirect pathological consequences of the disease, decreasing the rate of disease progression, amelioration or palliation of the disease state, and remission or improved prognosis.

In some examples, the alpha-synuclein aptamers described herein may be formulated in lipid particles.

Lipid particles include, but are not limited to, liposomes.

In some examples, a liposome is a structure composed of at least one lipid bilayer membrane that encloses an internal compartment. Liposomes may be characterized according to the membrane type and size. Small unilamellar vesicles (SUVs) have a single membrane and typically range between 0.02 and 0.05 pm in diameter; large unilamellar vesicles (LUVS) are typically larger than 0.05 pm. Oligolamellar large vesicles and multilamellar vesicles have multiple, usually concentric, membrane layers and are typically larger than 0.1 pm. Liposomes with several nonconcentric membranes, i.e., several smaller vesicles contained within a larger vesicle, are termed multivesicular vesicles.

Liposomes may be made of more or more different type of lipid's, depending upon, inter alia, intended use, ease of handling, cost, and the like.

In some examples, a liposome comprises a neutral, zwitterionic, cationic, and/or anionic lipids. As noted above, such lipids can be used alone or in combination.

The term "cationic lipid" refers to any amphiphilic molecule that is permanently positively charged at pH values within the range of 4.0 to 8.0.

The term "anionic lipid" refers to any amphiphilic molecule that is permanently negatively charged with at least one negative charge at pH values within the range of 4.0 to 8.0.

The term "neutral lipid" refers to cholesterol or any zwitterionic lipid.

The term "zwitterionic" refers to any amphiphilic molecule with net zero charge arising from the presence of both, positively and negatively, charged chemical groups at pH values within the range of 4.0 to 8.0.

Examples of neutral lipids include, but at not limited to, diacylphosphatidylcholine, diacylphosphatidylethanolamine, ceramide, sphingomyelin, dihydrosphingomyelin, cephalin, and cerebrosides.

Examples of cationic lipids include, but are not limited to, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), I-Linoleoyl-2-inoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DM A), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl-4-(dimethylamino) butanoate, N,N-dioleyl-N,N-dimethylammonium chloride ("DODAC"); N-(2,3-dioleyloxy)propyl-N,N—triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 1,2-Dioleyloxy-3-trimethylaminopropane chloride salt ("DOTAP.Cl"); 3.beta.-(N--(N',N'-dimethylaminoethane)-carbamoyl)cholesterol ("DC-Choi"), N-(I-(2,3-dioleyloxy) propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"), or mixtures thereof.

Examples of anionic lipids include, but are not limited to, phosphatidylglycerol, cardiolipin, diacylphosphatidylserine, diacylphosphatidic acid, N-dodecanoyl phosphatidylethanolamine, N-succinyl phosphatidylethanolamine, N-glutaryl phosphatidylethanolamine, lysylphosphatidylglycerol, and other anionic modifying groups joined to neutral lipids.

Amphipathic lipids include, but are not limited to, phospholipids, aminolipids, and sphingolipids. Examples of phospholipids include sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, or dilinoleylphosphatidylcholine. Other phosphorus-lacking compounds, such as sphingolipids, glycosphingolipid families, diacylglycerols, and β-acyloxyacids, can also be used.

A liposome may contain other elements including but not limited to: aptamers (e.g. in additional to the aptamers as described herein), antibodies, proteins, peptides, lipid derivatives; sterols, small molecules, and magnetic/paramagnetic particles. These may be used for various purposes. In some embodiments the complex to target specific cells/tissues, inducing antigen-specific immune responses in vivo and in vitro. In some examples these elements may or may not be PEGylated.

Sterols include, but are not limited to, cholesterol.

Additional components that may be present in a lipid particle include bilayer stabilizing components such as polyamide oligomers, peptides, proteins, detergents, lipid-derivatives, such as PEG coupled to a lipid, for example, PEG coupled to phosphatidylethanolamine and PEG conjugated to ceramides.

A lipid particle, such as a liposome, may also include a targeting moiety, for example a targeting moiety that is specific to a cell type or tissue. Targeting of lipid particles may be carried out using a variety of targeting moieties, such as ligands, cell surface receptors, glycoproteins, vitamins (e.g., riboflavin) and monoclonal antibodies. The targeting moieties can include the entire protein or fragments thereof. In some examples, targeting mechanisms generally require that the targeting agents be positioned on the surface of the lipid particle in such a manner that the targeting moiety is available for interaction with the target, for example, a cell surface receptor.

In one example, the targeting moiety is a transferrin receptor aptamer (TRA).

Additional and/or alternate targeting moieties include Carrier-mediated transport (CMT) including, but not limited to, glucose transporter 1 (GLUT1), Organic anion transporting polypeptide (OATP), large neutral amino acid transporter (LAT); receptor-mediated transport (RMT), including but not limited to, transferring receptor (TFR), insulin receptor (IR), lipoprotein receptor (LPR), diphtheria toxin receptor (DPTR).

Further, aptamers may be designed to target other components of the transport system of the blood brain barrier. See, for example, in Table 2 a listing of transport systems.

TABLE 2

| Transport system | Typical substrate | Transport rate |
|---|---|---|
| Metabolic substrates | | |
| Hexose | Glucose | 700 |
| Monocarboxylic acid | Lactate | 60 |
| Large neutral amino acid | Phenylalanine | 12 |
| Basic amino acid | Lysine | 3 |
| Acidic amino acid | Glutamate | 0.2 |
| β-amino acid | Taurine | 0.4 |
| Amine | Choline | 0.2 |
| Purine | Adenine | 0.006 |
| Nucleoside | Adenosine | 0.004 |
| Saturated fatty acid | Octanoate | |
| Vitamins and cofactors | | |
| Thiamine | Thiamine | |
| Pantothenic acid | Pantothenic acid | |
| Biotin | Biotin | |
| Vitamin $B_6$ | Pyridoxal | |
| Riboflavin | Riboflavin | |
| Niacinamide | Niacinamide | |
| Carnitine | Carnitine | |
| Inositol | myo-Inositol | |
| Electrolytes | | |
| Sodium | Sodium | 200 |
| Potassium | Potassium | 12 |
| Chloride | Chloride | 140 |
| Hormones | | |
| Thyroid hormone | $T_3$ | |
| Vasopressin | Arginine vasopressin | |
| Insulin | Insulin | |
| Other peptides | | |
| Transferrin | Transferrin | |
| Enkephalins | Leu-enkephalin | |

In one example, the liposome comprises one or more alpha-synuclein aptamers selected from SEQ ID NO: 1, SEQ ID NO: 2, SEQ ID NO: 3, SEQ ID NO: 4, or SEQ ID NO: 5.

In one example, the liposome comprises one or more alpha-synuclein aptamers selected from SEQ ID NO: 1, SEQ ID NO: 2, SEQ ID NO: 3, SEQ ID NO: 4, or SEQ ID NO: 5, and at least one targeting moiety.

In one example, the liposome comprises at least one alpha-synuclein aptamer selected from SEQ ID NO: 1, SEQ ID NO: 2, SEQ ID NO: 3, SEQ ID NO: 4, or SEQ ID NO: 5, and a targeting moiety, wherein the targeting moiety is a transferrin receptor aptamer.

In use, in one example, there is described a method of treating a subject having, or suspected of having, a neurodegenerative disorder, comprising: administering to a subject a liposome comprises one or more alpha-synuclein aptamers selected from SEQ ID NO: 1, SEQ ID NO: 2, SEQ ID NO: 3, SEQ ID NO: 4, or SEQ ID NO: 5.

In a specific example, the neurological disorder is Parkinson's disease (PD), dementia with Lewy bodies (DL), or multiple system atrophy (MSA).

In one example, the liposome comprises at least one alpha-synuclein aptamer selected from SEQ ID NO: 1, SEQ ID NO: 2, SEQ ID NO: 3, SEQ ID NO: 4, or SEQ ID NO: 5, and a targeting moiety, wherein the targeting moiety is a transferrin receptor aptamer.

It will be appreciated that in some examples, an aptamer is administered to a subject. In one example, a pharmaceutical composition comprising an aptamer is administered to a subject. A pharmaceutical composition may comprises an aptamer and a pharmaceutically acceptable excipient. In some examples a pharmaceutical composition comprising an aptamer as described herein may be used.

In one example, there is described a method of treating a subject having, or suspected of having, a neurodegenerative disease, comprising: administering at least one aptamer selected from SEQ ID NO: 1, SEQ ID NO: 2, SEQ ID NO: 3, SEQ ID NO: 4, or SEQ IDNO:5

In one example, there is described a method of treating a subject having, or suspected of having, a neurodegenerative disease, comprising: administering at least one aptamer selected from SEQ ID NO: 1, SEQ ID NO: 2, SEQ ID NO: 3, SEQ ID NO: 4, or SEQ ID NO: 5, and a pharmaceutically acceptable carrier.

In some examples, the neurodegenerative disease is Parkinson's disease (PD), dementia with Lewy bodies (DL), or multiple system atrophy (MSA).

In one example, subject is a human.

In use, in one example, there is described a method of treating a subject having, or suspected of having, a neurodegenerative disorder, comprising: administering to a subject pharmaceutical composition comprising at least one alpha-synuclein aptamer selected from SEQ ID NO: 1, SEQ ID NO: 2, SEQ ID NO: 3, SEQ ID NO: 4, or SEQ ID NO: 5. In a specific example, the neurological disorder is Parkinson's disease (PD), dementia with Lewy bodies (DL), or multiple system atrophy (MSA).

For in vivo administration, the aptamers, compositions pharmaceutical compositions, and/or liposomes comprising aptamers, may be administered topically, orally, and/or parenterally. In some example, administration is intraarticularly, intravenously, intraperitoneally, subcutaneously, or intramuscularly. In some examples, the pharmaceutical compositions are administered intravenously or intraperitoneally.

In some examples, the liposomes comprising an aptamer may be administered as is.

In some examples, the liposomes comprising an aptamer may be administered in a solution.

In some examples, the liposomes may be formulated to a suitable pharmaceutical composition to be administered by any desired route of administration.

Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages.

The pharmaceutical compositions may include the liposomes, a pharmaceutical acceptable excipient, and, optionally, may include other medicinal agents, pharmaceutical agents, carriers, adjuvants, and the like.

The phrase "pharmaceutically acceptable" as used herein means a pharmaceutically acceptable material, composition or vehicle, such as a liquid or solid filler, diluent, excipient, solvent or encapsulating material useful for formulating a drug for medicinal or therapeutic use. Each carrier must be "acceptable" in the sense of being compatible with other ingredients of the formulation and not unacceptably injurious to the patient.

In some example, the pharmaceutically acceptable carrier is inert to the nucleic acid encapsulated within the particles and which has no detrimental side effects or toxicity under the conditions of use.

In some examples, injectable formulations for parenteral administration may be prepared as liquid solutions or suspensions, solid forms suitable for solution or suspension in liquid prior to injection, or as emulsions. Suitable excipients include, but are not limited to, water, saline, dextrose, glycerol, ethanol or the like.

In some examples, the pharmaceutical compositions may also contain minor amounts of non-toxic auxiliary substances such as wetting or emulsifying agents, pH buffering agents and the like, such as for example, sodium acetate, sorbitan monolaurate, triethanolamine oleate, and the like.

In some examples, aqueous injection suspensions may also contain substances that increase the viscosity of the suspension, including, for example, sodium carboxymethylcellulose, sorbitol, and/or dextran. Optionally, the suspension may also contain stabilizers. The parenteral formulations can be present in unit dose or multiple dose sealed containers, such as ampules and vials, and can be stored in a freeze-dried (lyophilized) condition requiring only the addition of the sterile liquid carrier, such as, for example, water, for injections immediately prior to use. In some embodiments, parenteral administration includes intravenous administration.

In some examples, compositions for oral administration include, but are not limited to, solutions, suspensions, tablets, dispersible tablets, pills, capsules, powders, sustained release formulations and the like. Formulations suitable for oral administration can consist of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, (such as, for example ethanol, benzyl alcohol, and the polyethylene alcohols), either with or without the addition of a pharmaceutically acceptable surfactant, suspending agents, or emulsifying agents.

In some examples, the pharmaceutical preparations may be contacted with the target tissue by direct application of the preparation to the tissue. The application may be made by "topical", "open" or "closed" procedures. By "topical," it is meant the direct application of the pharmaceutical preparation to a tissue exposed to the environment. "Open" procedures are those procedures which include incising the skin of a patient and directly visualizing the underlying tissue to which the pharmaceutical preparations are applied. This is generally accomplished by a surgical procedure. "Closed" procedures are invasive procedures in which the internal target tissues are not directly visualized, but accessed via inserting instruments through small wounds in the skin. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

Combination Therapy

In some examples a neurodegenerative disease may be treated with a combination therapy, using an aptamer, pharmaceutical composition comprising an aptamer, or a liposome comprising an aptamer, together with an existing treatment of said neurodegenerative disease.

Thus, in some example, there is described a method and/or use of combination therapy. The term "combination therapy", as used herein, refers to those situations in which two or more different pharmaceutical agents are administered in overlapping regimens so that the subject is simultaneously exposed to both agents.

Combination therapy may be simultaneous treatment or sequential treatments.

In some example, there is provide a method of treating a subject having or suspect of having a neurodegenerative disease as described herein, and further comprising treating said subject with an existing treatment In some examples, dopamine agonists, for example, ropinirole (REQUIP®), pramipexole (MIRAPEX®), rotigotine (NEUPRO®), or/and Levodopa, may be used in the treatment of Parkinson's disease. Other examples may include trihexyphenidyl (ARTANE®) or benztropine (COGENTIN®) may be used. Selegiline (ELDEPRYL®, ZELAPAR®) and rasagiline (AZILECT®) may be used to block the break-down of dopamine.

In some examples, dopamine agonists, for example, ropinirole (REQUIP®), pramipexole (MIRAPEX®), rotigotine (NEUPRO®), or/and Levodopa, may be used in the treatment of dementia with Lewy bodies (DLB). Other examples may include trihexyphenidyl (ARTANE®) or benztropine (COGENTIN®) may be used. Selegiline (ELDEPRYL®, ZELAPAR®) and rasagiline (AZILECT®) may be used to block the break-down of dopamine.

In some examples, corticosteroids (e.g., fludrocortisone), pyridostigmine, midodrine, droxidopa, levodopa, carbidopa, and/or myeloperoxidase (MPO) inhibitors may be used in the treatment of multiple system atrophy (MSA).

Detection of Alpha-Synuclein Polypeptide in a Sample

In some examples, there is described a method of determining alpha-synuclein polypeptide in a sample The term "sample" or "biological sample," as used herein, refers to any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

In one example, said determination is in vivo determination.

In one example, said determination is in vitro determination.

As used herein "in vivo" refers to events that occur within a subject, such as a human and a non-human animal. In the context of cell-based systems, the term may be used to refer to events that occur within a living cell (as opposed to, for example, in vitro systems).

As used herein "in vitro" refers to events that occur in an artificial environment, for example, in a test tube or reaction vessel, in cell culture, etc., rather than within a subject.

In one example, there is described a method for detecting alpha-synuclein polypeptide in a biological sample, comprising: contacting said sample with an aptamer of any one of SEQ ID NO: 1, SEQ ID NO: 2, SEQ ID NO: 3, SEQ ID NO: 4, or SEQ ID NO: 4, said aptamer comprising a detectable label, and determining whether an increase in the detectable label, wherein an increase in the detectable label is indicative of the presence of alpha-synuclein polypeptide in the sample.

In one example, in the case of a "turn-off" sensor, a decrease in fluorescence measured may would be linearly related to the concentration of a syn measured. The detectable label may be quenched by the presence of the protein, for example.

The term "detectable label" as used herein refers to a chemical moiety that is directly or indirectly detectable (for example, due to its spectral properties, conformation or activity) when attached to a target or compound and used in the present methods, including reporter molecules, solid supports and carrier molecules. The detectable label can be directly detectable (fluorophore) or indirectly detectable (hapten or enzyme).

Detectable labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. Further, MRI contrast agent labelled aptamer, or CT agent labelled aptamer, may be used.

The term detectable label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a colorimetric substrate (e.g., tetramethylbenzidine (TMB)) or a fluorogenic substrate such as AMPLEX$^T$M Red reagent to detect the presence of HRP. Labels are known by those of skill in the art and include, but are not limited to, particles, fluorophores, haptens, enzymes and their colorimetric, fluorogenic and chemiluminescent substrates and other labels.

Diagnosis

In some example, there may be used a method of diagnosis. In one example, an aptamer as described herein may be labelled fluorescently. A subject showing early signs of a neurological disease may be injected with a fluorescently labelled aptamer. In one example, the neurodegenerative disease is a disease associate with alpha-synuclein. In some examples, the neurodegenerative disease is Parkinson's disease (PD), dementia with Lewy bodies (DLB), or multiple system atrophy (MSA). In some examples, the neurological disease is a synucleinopathy. In some examples, the neurological disease is associated with SNCA fibrillar aggregates, which may represent the major non A-beta component of Alzheimer disease amyloid plaque, and a major component of Lewy body inclusions. They are also found within Lewy body (LB)-like intraneuronal inclusions, glial inclusions and axonal spheroids in neurodegeneration with brain iron accumulation type 1.

In one example, in a subject having or suspected of having Parkinson's disease (for example, displaying motor symptoms of Parkinson's—tremor at rest), the subject is injected with the fluorescently labelled aptamer. A scan is run to determine the aptamer binding density in the brain.

In one example, if the aptamer is binding at a low level (optionally above a control without any pre-motor signs of Parkinson's or compared to a standard curve), this may mean there is potential for alpha-synuclein fibril formation but the protein aggregation is still at a preclinical level. At this point, treatment that impeded further aggregation may be initiated. In one example, treatment is with an aptamer of the present application. In the case of a more pronounced signal (or "high" signal) (optionally compared to a control or based on a standard curve), this may be reflective of a more advanced stage of Parkinson's (motor phase) and could benefit from treatments directed at reducing further aggregation in addition to treatments direct at symptoms management (e.g., L-DOPA).

Kits

Method of the invention are conveniently practiced by providing the compounds and/or compositions used in such method in the form of a kit. Such kit preferably contains the composition. Such a kit preferably contains instructions for the use thereof.

In one example, there is provided a kit comprising one or more aptamers that binds to alpha-synuclein protein, comprising:

a) a nucleic acid comprising or consisting of any one of α-syn-1(SEQ ID NO: 1), α-syn-2(SEQ ID NO: 2), α-syn-3(SEQ ID NO: 3), α-syn-4(SEQ ID NO: 4), or α-syn-5(SEQ ID NO: 5);

b) a nucleic acid having at least 70% sequence identity to the nucleic acid sequence of a);

c) a nucleic acid that hybridizes with the complementary strand of the nucleic acid of a);

d) a nucleic acid that differs from a) by one or more nucleotides that are substituted, deleted, and/or inserted; or e) a derivative of a), b), c), or d), and optionally instructions.

In one example, there is a provided a kit comprising one or more aptamers selected from SEQ ID NO: 1, SEQ ID NO: 2, SEQ ID NO: 3, SEQ ID NO: 4, SEQ ID NO: 5, and instructions for the use thereof In one example, said kit comprising a detectable label.

In one example, said kit comprising a targeting moiety.

In one example, said kit comprising a transferrin receptor aptamer.

In one example, said kit comprising a neutral lipid, an anionic lipid, a cationic lipid, and/or a zwitterionic lipid.

To gain a better understanding of the invention described herein, the following examples are set forth. It should be understood that these examples are for illustrative purposes only. Therefore, they should not limit the scope of this invention in anyway.

EXAMPLES

The present work focused on the development of a selection method, which allowed for the identification of DNA aptamers that bound selectively to alpha-synuclein monomer and prevented alpha-synuclein fibrilization.

Experimental Section:

Oligonucleotide Preparation

The oligonucleotides used in this work were prepared using standard phosphoramidite chemistry on a MerMade 6 DNA synthesizer (BioAutomation, Irving, Tex., USA). DNA phosphoramidites (dmf-dG-CE Phosphoramidite, dA-CE-Phosphoramidite, dT-CE Phosphoramidite, and Ac-dC-CE Phosphoramidite), modifiers (5'-fluorescein phosphoramidite (FAM) and spacer phosphoramidite 18 (HEG)) and DNA synthesis reagents (Activator, Cap A, Cap B, Deblock, Oxidizer) were purchased from Glen Research (Sterling, Va., USA). Biosynthesis reagent grade acetonitrile was purchased from VWR (Mississauga, ON, Canada). Cleavage of the synthesized DNA from the 1000 Å controlled pore glass (CPG) columns was done in ammonium hydroxide at 55° C., overnight. Oligonucleotides were purified using polyacrylamide gel electrophoresis (PAGE), desalted using Amicon Ultra Centrifugal Filter Units (3 K NMWL, 0.5 mL: Millipore, Billerica, Mass., USA), and quantified using UV-Visible spectroscopy. The DNA library prepared for the selection experiment contained was derived from two templates. The novel (5'-ATAGTCCCATCATTCATT-N30-AGATATTAGCAAGTGTCA-3') (SEQ ID NO: 6) and mutant pools were prepared separately but contained identical 5'- and 3'-primer regions. The mutant pool was based on the M5-15 aptamer, which had been previously selected to bind to alpha-synuclein.[17] The sequence of the M5-15 aptamer was 5'-atagtcccatcattcat-tGTATGGTACGGCGCGGTGGCGGGTGCGTGGagatatt-agcaagtgtca-3' (SEQ ID NO: 7) where the primer domains are shown in lower case letters and the bases mutated by 30% are shown in capital letters. The primers used for polymerase chain reaction (PCR) in the selection experiment were as follows: 5'-FAM-ATAGTCCCATCATTCATT (forward) (SEQ ID NO: 8) and 5'-AAAAAAAAAAAAAAAAAAAA-HEG-TGACACTTGCTAATATCT (reverse) (SEQ ID NO: 9).

Selection of Aptamers by Modified SELEX

Selection Conditions

The DNA selection library and alpha-synuclein were prepared separately in selection buffer (PBS: 137 mM NaCl, 2.7 mM KCl, 8.1 mM $Na_2HPO_4$, 1.8 mM $KH_2PO_4$). To incubate the target with the selection library, an equimolar reaction was prepared. Alpha-synuclein aggregation controls containing no DNA were prepared in selection buffer. To increase stringency and selective pressures, the amount of DNA and protein were varied. The buffer pH and incubation times were also varied. These parameters are summarized in Table 3.

TABLE 3

| Round | Buffer pH | DNA and protein concentration (μM) | Incubation length (days) |
|---|---|---|---|
| 1 | 7.2 | 30 | 2 |
| 2 | 7.2 | 16.5 | 5 |
| 3 | 7.2 | 7 | 5 |
| 4 | 6.5 | 7 | 4 |
| 5 | 6.5 | 7 | 13 |

The first selection round contained only novel pool. The selection library was spiked with M5-15 starting at the second round of selection. To induce aggregation, the incubation reaction in round 1-3 was flash-frozen in liquid nitrogen then lyophilized overnight using a Labconco lyophilizer (Fisher Scientific, Ottawa, ON, Canada). The dried reaction was then suspended in 180 μL of deionized water obtained directly from a Milli-Q deionized water (18 MΩ cm) unit (Millipore) and placed on an incubator (180 RPM at 37° C.). Selection rounds 4 and 5 were placed directly on the incubator after preparation. The incubation time for each round is summarized in table 2.

Fractionation by Ultracentrifugation

Following the DNA library-target incubation period, free DNA and protein-bound DNA were partitioned based on the molecular weight using ultracentrifugation. A density gradient was prepared using OPTIPREP™ (Sigma-Aldrich, St. Louis, Mo., USA), selection buffer and deionized water. Density gradients were created by layering different percent solutions of OPTIPREP™ in 5 mL thermal sealing ultracentrifuge tubes (Beckman, Brae, Calif., USA). In the first round of selection the density gradient was created by layering 35% (0.71 mL), 25% (2.14) and 2.5% (2.4 mL). The density gradient for round 2 was created by layering 35% (1.0 mL), 25% (1.0 mL), 12% (1.0 mL), 6% (1.0 mL), 2.5% (1.0 mL), and 1% (0.6 mL). Similarly, the density gradients for rounds 3, 4, and 5 were created by layering 35% (1.0 mL), 25% (1.0 mL), 20% (1.0 mL), 12% (1.0 mL), 6% (1.0 mL), and 2.5% (0.6 mL). After the density gradient was prepared, the incubation reaction was loaded on top of the density gradient and the tubes were sealed (Beckman Tube Sealer). A protein ladder control (PRECISION PLUS PROTEIN™ All Blue Standard: Bio-Rad Laboratories, Hercules, Calif., USA) was also used to optimize the OPTIPREP™ gradient between rounds. The reactions were centrifuged as described in Table 4.

TABLE 4

| Round | Centrifugal Force (x g) | Time (h) |
|---|---|---|
| 1 | 50 000 | 1 |
| 2 | 100 000 | 20 |
| 3 | 100 000 | 7 |
| 4 | 100 000 | 5.5 |
| 5 | 100 000 | 6 |

Following centrifugation, 200 μL (rounds 1 and 2) or 250 μL (rounds 3-5) fractions were collected from the top of the tube. The location of free DNA, and DNA bound to different protein aggregate masses was estimated by measuring the fluorescein labeled DNA fluorescence with excitation and emission wavelengths of 494 nm and 520 nm respectively (FLUOROLOG®, Horiba Jobin Yvon Inc., Edison, N.J., USA) of each fraction. Additionally the location of a protein ladder control treated to the same gradient was analyzed by 5% non-denaturing PAGE to provide information about the molecular mass corresponding to each fraction. The fluorescent DNA and protein were visualized in the non-denaturing polyacrylamide gel by excitation of the fluorescein at 302 nm, and staining with Stains-All (Sigma-Aldrich) respectively. These data combined were used to determine several fractions of interest; those being unbound DNA, and DNA bound to monomer, oligomer and aggregate.

Secondary Incubation

To apply further selective pressure, a secondary incubation period was employed after fractionation, and prior to characterization by transmission electron microscopy. This allowed the inhibitory effect of the selection library on protein aggregation to be assessed by TEM imaging. The length of the secondary incubation period was also varied by round. The secondary incubation periods for round 2, 3, and 4 were 130 hours (at 4° C.), 4 hours (room temperature), 48 hours (room temperature) respectively.

Characterization by Transmission Electron Microscopy (TEM)

Following fractionation by ultracentrifugation, electron microscopy was used to assess the protein morphology present in each fraction of interest. Carbon coated copper grids (CF300-Cu: Electron Microscopy Sciences, Hatfield, Pa., USA) were prepared for imaging by depositing 4 μL of each fraction. After 10 min the excess sample was removed and the grids were allowed to dry. Transmission electron microscopy images were obtained using a FEI Tecnai G2 F20 Transmission Electron Microscope (Hillsboro, USA) equipped with a Gatan ORIUS TEM CCD Camera (Pleasanton, USA) imaging system. Images were obtained using a beam voltage of 120 kV. Elemental analysis by energy dispersive spectroscopy using an Oxford AztecTEM with 80 mm elemental silicon drift detector (SDD) and a take off angle of 20° was performed to confirm the presence of protein and DNA.

Partitioning of DNA-Bound Protein by Nitrocellulose Filtration

To isolate the highest affinity sequences from those which bound to the monomer protein, nitrocellulose filtration was employed following the secondary incubation. Nitrocellulose filters (0.45 µm HA: Millipore) were pretreated by soaking in 1 mL of 0.5 M KOH for 20 minutes while shaking. The filters were washed with 4×100 mL of deionized water. Fractions of interest were filtered by passing a 200 µL sample volume over the pretreated membrane using a SWINNEX™ filter mount (Millipore) attached to a 1 mL syringe. The filter was removed and the retained DNA-protein complexes were eluted in 1 mL of urea elution buffer (7 M Urea, 0.05 M HEPES, pH 7.5). The filters were vortexed in elution buffer for 20 min then heated to 95° C. for 15 min. The filter was removed and discarded.

Recovery of Binding DNAs by Phenol-Chloroform Extraction and Ethanol Precipitation To separate the DNA from the protein in solution, an equal volume of phenol:chloroform, isoamyl alcohol (25:24:1; BioShop Canada Inc., Burlington, ON, Canada) was added to the eluate. The solution was vortexed briefly then centrifuged (12 000×g) for 5 min. The aqueous layer was removed, and extracted as described an additional 2 times with fresh equivolume aliquots of phenol:chloroform, isoamyl alcohol. To remove residual phenol from the aqueous layer, a chloroform extraction was performed.

DNA was recovered by ethanol precipitation. Briefly, 100 µL of sodium acetate was added to the aqueous phase. After vortexing the sample, 2.75 mL of ethanol pre-chilled on ice was added to the aqueous phase. The solution was briefly vortexed, placed on ice for 20 minutes, then centrifuged (12 000×g) for 15 min. The supernatant was removed and the pellet was resuspended in 500 µL of deionized water then desalted using AMICON® Ultra Centrifugal Filter Units (3 K NMWL, 0.5 mL: Millipore, Billerica, Mass., USA). The presence of DNA following recovery by phenol:chloroform extraction and ethanol precipitation was confirmed using fluorescence spectroscopy.

Amplification of the Selection Library by Polymerase Chain Reaction (PCR)

Binding DNAs were amplified by PCR. After each selection round, 60 PCR reactions were prepared to amplify the enriched library. Negative (which did not include template DNA) and positive (which included template DNA) control reactions were also prepared. The PCR mastermix contained the reagents in the following proportions (for 15 reactions): 750 µL of 2×Flumag Buffer (100 mM KCl, 200 mM Tris, 2% triton x-100, pH of 9.0), 555 µL of deionized water, 120 µL of $MgCl_2$, 30 µL of dNTPs (BioShop Canada Inc.), 7.5 µL of the each of the 0.2 mM primer solutions. Finally, 15 µL of TAQ DNA polymerase (BioShop Canada, Inc.) was added to the mastermix and the solution was mixed gently by repeated pipetting. PCR reactions were prepared by aliquoting 99 µL of the mastermix into each tube, then adding 1 µL or either pool, water or template. PCR was performed using an thermal cycler (Eppendorf) using the following thermal program: 94° C. (10 min), 30×[94° C. (1 min), 47° C. (1 min), 72° C. (1 min)], 72° C. (10 min), then finally 4° C. (10 min). The PCR product was purified by denaturing gel electrophoresis using 12% acrylamide gels. The forward primer was fluorescently labeled which allowed for the visualization of the selection library by fluorescence excitation at 302 nm. The reverse primer was extended with a poly A20 tail, which allowed for sufficient separation of the selection library and its complement by length. The library was eluted from the crushed gel into deionized water overnight, then desalted using AMICON® Ultra Centrifugal Filter Units (3 K NMWL, 0.5 mL: Millipore, Billerica, Mass., USA) and subsequently quantified by UV-Visible spectroscopy.

High Throughput Sequencing (HTPS) and Computational Analysis of Selection Data

MiSeq Sequencing

Select positive, negative and counter pools were sequenced using high throughout sequencing technology. The pools were prepared for HTPS via amplification with specially designed forward and reverse primers. The primers contained barcode regions, which allowed for the sequencing of multiple pools in one experiment. The primer sequences used are shown in table 4.

Table 5: Forward (F) and reverse (R) primer sequences used for Illumina MiSeq HTPS. Primer regions that were complementary to the original template are bolded. Illumina MiSeq barcode adapters are underlined.

TABLE 5

| Primer Name | Sequence (5'→3') |
|---|---|
| F1 | AATGATACGGCGACCACCGAGATCTACACTCTTTCCCTACACGACGCTCTTCCGATCTTATAGTCCCA TCATTCATT (SEQ ID NO: 10) |
| F2 | AATGATACGGCGACCACCGAGATCTACACTCTTTCCCTACACGACGCTCTTCCGATCTNATAGTCCC ATCATTCATT (SEQ ID NO: 11) |
| F3 | AATGATACGGCGACCACCGAGATCTACACTCTTTCCCTACACGACGCTCTTCCGATCTNNATAGTCC CATCATTCATT (SEQ ID NO: 12) |
| F4 | AATGATACGGCGACCACCGAGATCTACACTCTTTCCCTACACGACGCTCTTCCGATCTNNNATAGTC CCATCATTCATT (SEQ ID NO: 13) |
| R1 | CAAGCAGAAGACGGCATACGAGAT<u>CGTGAT</u>GTGACTGGAGTTCAGACGTGTGCTCTTCCGATCTTG ACACTTGCTAATATCT (SEQ ID NO: 14) |
| R2 | CAAGCAGAAGACGGCATACGAGAT<u>ACATCG</u>GTGACTGGAGTTCAGACGTGTGCTCTTCCGATCTTG ACACTTGCTAATATCT (SEQ ID NO: 15) |
| R3 | CAAGCAGAAGACGGCATACGAGAT<u>GCCTAA</u>GTGACTGGAGTTCAGACGTGTGCTCTTCCGATCTNT GACACTTGCTAATATCT (SEQ ID NO: 16) |

TABLE 5-continued

| Primer Name | Sequence (5'→3') |
|---|---|
| R4 | CAAGCAGAAGACGGCATACGAGAT<u>TGGTCA</u>GTGACTGGAGTTCAGACGTGTGCTCTTCCGATCTNT GACACTTGCTAATATCT (SEQ ID NO: 17) |
| R5 | CAAGCAGAAGACGGCATACGAGAT<u>CACTGT</u>GTGACTGGAGTTCAGACGTGTGCTCTTCCGATCTNNT GACACTTGCTAATATCT (SEQ ID NO: 18) |
| R6 | CAAGCAGAAGACGGCATACGAGATA<u>TTGGC</u>GTGACTGGAGTTCAGACGTGTGCTCTTCCGATCTNNT GACACTTGCTAATATCT (SEQ ID NO: 19) |
| R7 | CAAGCAGAAGACGGCATACGAGAT<u>GATCTG</u>GTGACTGGAGTTCAGACGTGTGCTCTTCCGATCTNNNT GACACTTGCTAATATCT (SEQ ID NO: 20) |
| R8 | CAAGCAGAAGACGGCATACGAGAT<u>TCAAGT</u>GTGACTGGAGTTCAGACGTGTGCTCTTCCGATCTNNNT GACACTTGCTAATATCT (SEQ ID NO: 21) |

The PCR mastermix and reactions were prepared as described for SELEX with the exception that the elongated primer pairs were used where appropriate. The thermal profile used during amplification was 94° C. (10 min), 17×[94° C. (1 min) 58-60° C. (1 min), 72° C. (1 min)], 72° C. (10 min), then finally 4° C. (10 min). The PCR product was purified on a 12% polyacrylamide denaturing gel, desalted as previous described and then quantified using a NANODROP™ 1000 Spectrophotometer (Thermo Fisher, Waltham, Mass., USA). The sequencing experiment was performed on an Illumina MiSeq Instrument (Illumina, San Diego, Calif., USA) according to the technical document provided by Ilumina for MiSeq sequencing with the exception that the PhiX amount used was increased from the recommended value of ≥5% to 20%.This increase was necessary since the diversity of the starting DNA was low. The MiSeq® Reagent Kit v2 (300 cycle) kit and PhiX CONTROL V3KIT required were purchased from Illumina.

Analysis of Sequencing Data Using AptaCluster

Sequencing data were exported from the MiSeq Illumina System as FASTQ formatted files to BASESPACE® (Illumina, Inc., San Diego, CA). The AptaTools software suite developed by Przyrycka and colleagues was used to analyze the sequencing data.[19, 20] A configuration file was prepared according to the AptaCLUSTER manual available online: ncbi.nlm.nih.gov/CBBresearch/Przytycka/index.cgi#aptaclustermanual. From the analyses, data including the raw sequence count, the pool fraction and selection cycle-to-cycle enrichment was shown for each sequence. From these data, five aptamer candidates were identified.

Screening of Aptamer Candidates for their Inhibition of Alpha-Synuclein Aggregation Screening of Aptamer Candidates for their Inhibitory Effect on Alpha-Synuclein Aggregation Under Selection Conditions (5 Days)

Aptamer candidates and alpha-synuclein monomer were prepared in selection buffer and combined in a 1:1 ratio to a final concentration of 3.5 µM in a volume of 340 µL. As a control, a reaction containing the M5-15 aptamer was also prepared. To mimic the conditions of the selection, the incubation reactions were placed on an incubator/shaker at 37° C. and 180 RPM for 125 hours. Following the incubation period the reactions were subjected to ultracentrifugation using the following density gradient prepared as described for the selection: 35% (1.0 mL), 25% (1.0 mL), 20% (1.0 mL), 12% (1.0 mL), 6% (1.0 mL) and 2.5% (0.6 mL). The incubation reactions were centrifuged at 100 000×g for 6 h. Fractions (1 mL) were collected and the protein morphologies in fractions of interest were examined by TEM described for the selection.

Screening of Aptamer Candidates for their Inhibitory Effect on Alpha-Synuclein Aggregation According to the MJFF Protocol for the Formation of Fibrils (7 Days)

To investigate the ability of the aptamer candidates to specifically prevent fibril formation, aptamer and alpha-synuclein monomer were combined in 1× Dulbecco's PBS (Sigma-Aldrich) to produce a final concentration of ~5 mg/mL of each component. Aliquots (41 µL) of alpha-synuclein monomer for Pre-Formed Fibrils (PFFs) at approximately 5 mg/mL (346 µM) were pipetted into 1.5 mL amber microcentrifuge tubes to prepare 7 reactions, one for each of the aptamer candidates, an M5-15 aptamer control and an alpha-synuclein control. For each reaction, a small volume (7-9 µL) of concentrated aptamer stock solution was added to yield a final concentration of 346 µM and was diluted to a final volume of 50 µL using 1×PBS. This created a final concentration ratio of 1.2 aptamer:1 alpha-synuclein. The incubation reactions were vortexed briefly then placed on an incubator/shaker at 37° C. and 300 RPM for 7 days. On each day, aliquots were removed for TEM imaging and assessment of fibril formation by the Thioflavin T assay. The preparation of grids and TEM imaging were done as described for the selection experiment.

Thioflavin T Assay

A 1 mM Thioflavin T (Sigma-Aldrich) stock solution was created by dissolving 0.0128 g of Thioflavin T into 40 mL of 1×PBS. For the assay, a working solution of 25 µM Thioflavin T stock was prepared by combining 25 µL of stock solution and 975 µL of 1×PBS. 2.5 µL of each incubation reaction was combined with 95 µL of the Thioflavin T working solution and allowed to incubate at room temperature for 3 min, and then diluted 1:10 using 1×PBS. The samples incubated for an additional hour at room temperature before fluorescence readings were taken using a fluorescence spectrometer (Horiba Jobin Yvon, Edison, N.J., USA). Samples were excited at 440 nm and the emission spectra were examined between 470 nm and 600 nm.

Assessment of the Inhibitory Effect of a-Syn-1 on Alpha-Synuclein Aggregation

Longitudinal Study of the Inhibitory Effect of a-Syn-1 on Alpha-Synuclein Aggregation Under Selection Conditions (25 Days)

To examine the specific inhibitory effect of a-syn-1 on alpha-synuclein aggregation over time, each component was combined in a 1:1 ratio (20 µM final concentration of each component) in selection buffer at near physiological pH (7.3). Controls of alpha-synuclein alone (20 µM), and alpha-synuclein combined in a 1:1 ratio (20 µM) with the M5-15 aptamer were also prepared. The incubation reactions were placed on an incubator shaker at 37° C. and 180 RPM for 25 days. After 4 days, 8, days, 10 days and 25 days aliquots were removed to prepare grids for TEM imaging as described in the selection section. To get a global indication of protein morphology, samples were prepared for TEM imaging without having undergone fractionation by ultracentrifugation at each time point.

Assessment of Aptamer Binding Affinity In Vitro
Microscale Thermophoresis

As an initial assessment of in vitro binding affinity of the aptamer candidates for alpha-synuclein, microscale thermophoresis (MST) was employed. Aptamer candidates (5 µL of 100 µM) dissolved in 1×Dulbecco's PBS, dry alpha-synuclein monomer protein, and excess PBS buffer were sent to Thomas Schubert at 2Bind (Germany) who performed the assessments. Sequences were assessed for binding using a constant aptamer candidate concentration (50 nM). Serial dilutions of the target, alpha-synuclein protein were prepared at concentrations that ranged from 300 µM to ~350 µM. In the experiment, an equivolume (either 3 µL or 4 µL) of the aptamer candidate and protein that had been prepared in 1×PBS buffer containing 0.05% Tween-20 were combined. Samples were analysed using a Monolith NT.115 Pico at 25° C. which had 5% LED power and 80% laser power.

DNase I Assay

A serial dilution of alpha-synuclein was prepared from a 5 mg/mL stock solution of a-syn monomer using 1×Dulbecco's PBS (Sigma-Aldrich). The concentrations were: 30 µM, 3 µM, 0.6 µM, 0.12 µM, 0.024 µM, 0.0048 µM. A volume of 20 µL of each alpha-synuclein dilution was combined with 20 µL of 10 µM 5'-fluorescein-labelled aptamer and the samples were incubated at 37° C. for 1 h with steady shaking. Additionally, two solutions containing 20 µL of 10 µM aptamer and 20 µL of 1×PBS were mixed and incubated at 37° C. for 1 h as controls. After incubation, the alpha-synuclein dilution series and one of the aptamer dilutions were treated with DNase I (Sigma-Aldrich) for 15 minutes at room temperature and were mixed briefly. An equivalent volume of formamide was added to each solution and then the solutions were loaded onto a multi-lane 19% denaturing polyacrylamide gel and 1×TBE (0.089 M Tris, 0.089 M Boric Acid, 0.002 M EDTA) running buffer was used. The gel apparatus was run at 300V for 3.5 hours. The gel was imaged using an ALPHAIMAGER™ and the images were analysed using the SpotDenso feature of the ALPHAIMAGER™ software. By comparing the relative fluorescence of the respective bands in each lane, a binding isotherm was generated from which an apparent dissociation constant was approximated. The standard curve analysis (four parameter logistic curve) feature of SigmaPlot (Version 10.0: Systat Software, Inc.) was used to fit the relative fluorescence data based on the following equation;

$$y = \min + \left((\max - \min)\Big/\left(1 + \left(\frac{x}{EC50}\right)^{Hillslope}\right)\right)$$

Equation X: Four parameter logistic curve where y=relative fluorescence, x=alpha-synuclein concentration, min=minimum relative fluorescence value that can be obtained, max=maximum relative fluorescence value that can be obtained, EC50 is the point of inflection of the curve, Hillslope=corresponds to the steepness of the curve at the inflection point The predicted EC 50 value was taken as an estimation of the apparent KD.21 The reported apparent dissociation constant represents the average of three bands and the error represents the standard deviation between the predicted values of the apparent KDs.

Preparation of a-Syn-1 Aptamer Loaded-Transferrin Receptor Aptamer Modified Liposomal Delivery Vehicle (a-Syn-TRAM)

Stock solutions of lipids for the production of liposomes were created by dissolving the following substrates in chloroform: 100 mg of POPC (16:0 18:1 PC Palmitoyloleoylphosphatidylcholine) was dissolved in 8 mL of chloroform, 1 mg of DDAB (Didodecyldimethylammonium bromide) was dissolved in 1 mL of chloroform, and 1 mg DSPE-PEG 2000 (1,2-distearoyl-sn-glycero-3-phosphoethanolamine-N-[amino(polyethylene glycol)-2000] (ammonium salt)) was dissolved in 1 mL of chloroform.

1.17 mL (19.2 µmol) of the POPC stock solution, 126.3 µL (273 nmol) of the DDAB stock solution, and 88.25 uL (30 nmol) of the DSPE-PEG 2000 maleimide (1,2-distearoyl-sn-glycero-3-phosphoethanolamine-N-[maleimide (polyethylene glycol)-2000](ammonium salt)) stock solution were transferred into a 10 mL round bottom flask containing 1.7 mg (606 nmol) of DSPE-PEG 2000. The flask was capped with a septum and placed under a steady flow of argon along with gentle shaking to evaporate the chloroform and produce a thin uniform lipid film. The lipid film was hydrated with 0.2 mL of 50 mM TRIS-HCl, at pH 7.0, and vortexed for 30 min. The flask was stored under argon and sonicated in a bath sonicator at room temperature for 10 min. 38 nmol of 5'-Cyanine 3.5-labelled a-syn-1 aptamer was added to the flask in a volume of 0.2 mL using 50 mM TRIS-HCl, at pH 7.0. To encapsulate the aptamer, 0.6 mL of 67% ethanol was slowly added to the flask; this yields a final concentration of 40% ethanol in solution. The flask was stored under argon and underwent 10 freeze-thaw cycles by undergoing 5 minutes in an ethanol/dry ice bath and 2 minutes in a 40° C. water bath per cycle. Following the final freeze-thaw cycle, the liposome samples were extruded by undergoing 25 passes through a 100 nm polycarbonate membrane in a mini-extruder. The samples were dialysed using 20000 Molecular Weight Cut-Off SLIDE-A-LYSER™ cassettes (Thermo Scientific) into 50 mM HEPES buffer, at pH 7.0, overnight. To remove DNA which was non-specifically interacting with the liposome exterior, nuclease digestion was performed using DNase I (Sigma-Aldrich) for 10 minutes. The samples were dialysed into 50 mM HEPES buffer, at pH 7.0, overnight to remove the digested DNA from the samples. 120 nmol of thiol-modified transferrin receptor aptamer (TRA) was combined with 75 µL of 50 mM TRIS-HCl, at pH 8.4, containing 100 mM DL-dithiothreitol (DTT) and vortexed at room temperature to cleave the disulfide bond on the TRA. Following the thiol cleavage, the TRA was purified using biospin columns (Bio-Rad Laboratories) then buffer exchanged into 50 mM HEPES buffer, at pH 7.0, containing 7 mM EDTA. The TRA solution was added to the liposome suspension and allowed to react with the maleimide group on the liposome at room temperature with gentle shaking. The samples were dialysed overnight into 50 mM HEPES buffer, at pH 7.0, to remove the EDTA and unreacted TRA.

The aptamer concentration was characterized using UV-Vis spectroscopy to maintain consistency between samples. To determine an approximate aptamer concentration, the Cyanine 3.5 peak, 590 nm, was observed with a 1:10 dilution of the liposome sample. The size distribution of the liposomes was characterized using TEM microscopy. Quantification of the phospholipid concentration was performed using the Stewart Assay.

Stewart Assay

A standard lipid solution was created using the stock solutions from the liposome synthesis; 1.17 mL (19.2 µmol) of the POPC stock solution, 126.3 µL (273 nmol) of the DDAB stock solution, and 88.25 µL (30 nmol) of the DSPE-PEG 2000-maleimide stock solution were transferred to a vial containing 1.7 mg (606 nmol) of DSPE-PEG 2000 (1,2-distearoyl-sn-glycero-3-phosphoethanolamine-N-[amino(polyethylene glycol)-2000](ammonium salt)). This standard solution was diluted to 0.1 mg/mL using chloroform in order to fit within the bounds of the assay. 10 mL of ferrothiocyanate solution was created using 0.2702 g (1 mmol) of Iron (Ill) chloride hexahydrate (Sigma-Aldrich) and 0.3041 g (4 mmol) of ammonium thiocyanate (Sigma-Aldrich). A concentration gradient of the diluted lipid standard (from blank (0 mg/mL) to 0.05 mg/mL) was developed in triplicate and mixed with an equal volume of the ferrothiocyanate solution. To analyze the liposomes, a 1:100 dilution of the final TRA-conjugated (a-syn-TRAM) liposome (transferrin aptamer modified liposome containing a-syn aptamer) solution was mixed with an equal volume of ferrothiocyanate solution. The solutions were vortexed for 15 seconds and then centrifuged at 1000 rpm for 5 minutes. Centrifugation produced a lower chloroform layer and an upper aqueous layer. The chloroform layer was removed using a pipette and analyzed at 485 nm using a Cary 300 Bio UV-Vis spectrophotometer (Agilent, Santa Clara, Calif., USA). The liposome solution was too concentrated for the assay and it was diluted 1:1 with chloroform for UV-Vis analysis.

Animal Experiments

Subjects

Approval, in accordance with the guidelines set by the Canadian Council on Animal Care (CCAC), was provided by the Carleton University Animal Care Committee for all of the animal procedures described in this work. The A53T alpha-synuclein transgenic line M83 (B6;C3-Tg(Prnp-SNCA*A53T)83Vle/J) commercially available from The Jackson Laboratory (Bar Harbor, Me., USA) were used. (Giasson, B. I., Duda, J. E., Quinn, S. M., Zhang, B., Trojanowski, J. Q., Lee, V. M. Neuronal alpha-synucleinopathy with severe movement disorder in mice expressing A53T human alpha-synuclein. Neuron 34, 521-533 (2002).) This model over-express the human A53T variant alpha-synuclein and animals exhibit symptoms of progressively severe motor impairment at approximately 8-14 months. A breeding colony was established between 2 pairs of male hemizygous for Tg(Prnp-SNCA*A53T)83Vle and female hemizygous for Tg(Prnp-SNCA*A53T)83Vle. The genotypes (WT, Tg1x, or Tg2x) of the animals were confirmed using DNA extracted from ear punches. Animals were housed in 27×21×14 cm clear, polycarbonate cages in a vivarium that was temperature (19-22° C.) and humidity (50-60%) controlled. Environment lighting was on a constant 12 hour dark/light cycle with lights on at 08:00. Animals were fed mice chow (Purina), and given water, ad libitum.

Characterization of Alpha-Synuclein Distribution in the A53T Alpha-Synuclein Transgenic Line M83 Mouse Model Immunohistochemical Evaluation of Alpha-Synuclein Distribution in the A53T Alpha-Synuclein Transgenic Line M83 Mouse Model To examine the changes in alpha-synuclein distribution over time, mice (n=3) from each genotype (WT, Tg1x, Tg2x) were euthanized at 3, 5 and 6 months. The distributions of alpha-synuclein at each age, and in each genotype were examined immunohistochemically by staining brain tissue with an anti-alpha-synuclein (phosphor S129) antibody (ab59264: abcam, Toronto, ON, Canada). Briefly, 60 µm coronal sections were washed 3 times in T-PBS for 5 minutes per wash then incubated in 0.3% hydrogen peroxide/T-PBS for 30 min to remove endogenous peroxidase activity. Sections were washed 3 more times in T-PBS for 5 minutes per wash, transferred into 1× animal free blocker (AFB; Vector Laboratories) in T-PBS for 60 minutes then incubated overnight at room temperature in the rabbit polyclonal antibody to Alpha-synuclein (phospho S129) (1:5000; Abcam)) in 1×AFB/T-PBS. This antibody detects endogenous levels of Synuclein only when phosphorylated at serine 129. Phosphorylation of Ser-129 is selective and extensive in synucleinopathy lesions. In vitro, phosphorylation at Ser-129 promotes insoluble fibril formation.

The following day, tissue was washed 3 times in T-PBS for 5 minutes per wash then incubated for 2 hours with a biotinylated goat anti-rabbit secondary antibody (1:500; Vector Laboratories) in 1×AFB/T-TBS. Sections were washed 3 times for 5 minutes each wash in T-PBS then incubated in an avidin biotin complex (ABC; Vector Laboratories) in T-PBS for 1 hour. Sections were rinsed three times in TBS for 5 minutes each and staining was visualized with a nickel-ammonium enhanced 0.5%, 3,3'-diaminobenzene (DAB; Sigma-Aldrich) solution. Sections were washed in TBS for 5 minutes then mounted onto glass slides.

Visualization of Aptamer Binding in Ex Vivo Brain Tissue from A53T Alpha-Synuclein Transgenic Line M83 Mice by Fluorescence Microscopy Animals (n=12; 6 males and 6 females) were injected with 0.1 mL of the a-syn-TRAM liposomes. After 30 minutes, animals were sacrificed by live decapitation. Brain tissue was collected, and immediately frozen on dry ice. Binding of the a-syn-1 aptamer to alpha-synuclein was investigated by examining the co-localization of the anti-alpha-synuclein (phosphor S129) antibody and the bound Cy3.5 labelled a-syn-1 aptamer on ex vivo tissue slices using fluorescence microscopy.

Inhibition of Alpha-Synuclein Aggregation In Vivo by a-Syn-1

To investigate the inhibitory effect of a-syn-1 aptamer delivered by a-syn-TRAM to the brain of A53T alpha-synuclein transgenic line M83 mice over time, a repeated injection study was carried out. Four month old male Tg2x mice (n=2) were injected with 0.1 mL of a-syn-TRAM for 3 consecutive days, 3 months in a row, for a total of 9×0.1 mL injections. Injections were spaced 1 month apart. Animals were sacrificed by rapid decapitation following the 9th injection. Brain tissue was collected and the distribution of the aptamer was examined by fluorescence microscopy as previously described.

The inhibition of alpha-synuclein oligomer and fibril formation by a-syn-1 was assessed using immunohistochemistry. Tissue from the motor cortex was collected at the time of sacrifice, when animals were 6 months old, was stained with anti-alpha synuclein (phosphor S129) antibody. Age-matched controlled were also examined. The number of alpha-synuclein positive cells was quantified using ImageJ Particle Analysis function. Images were threshold adjusted to ensure that only alpha-synuclein positive cells were set apart from background. The pixel size for objects to be counted ranged from 50-200 and roundness value was set between 0.75 and 1 (1 being a perfect circle). These settings maximized the chances of only counting round objects with a high grey value which, by visual inspection, were alpha-synuclein-stained cells. Counts were carried out over the same area for all sections. Statistical differences between the groups were examined using a T-test with α=0.05.

DISCUSSION

Described herein, inter alia, is the selection of novel aptamers that bind to the alpha-synuclein monomer protein both in vitro and in vivo, and inhibit oligomerization to larger order aggregates of the protein. The first step of the selection was the preparation of a DNA selection library. The aptamer selection experiment used a DNA selection template that consisted of a central random region (30 bases long) which was flanked on the 5'-end and 3'-end with known primer regions. To add complexity to the starting library and to also increase the likelihood of selecting aptamers with high affinity to the aptamer target, alpha-synuclein monomer, an existing aptamer (M5-15) that had been previously selected by Tsukakoshi et al., (2010) was also incorporated into the selection library. The M5-15 aptamer was synthesized with a 30% mutation to the original random region domain. Once the requisite DNA had been prepared, the selection procedure that we designed to find fibrilization inhibitors worked as follows. Alpha synuclein protein was incubated with the DNA library under conditions that are thought to encourage aggregation. Ultracentrifugation was then used to fractionate the samples by size and the lightest fractions that were thought to contain aptamer and alpha synuclein were retained. These fractions were then once again allowed time to aggregate. The hypothesis was that the oligonucleotides within this fraction inhibit the aggregation of the alpha synuclein protein to which they are bound, while oligonucleotides found in other heavier fractions lack that inhibitory ability.

Since the selection method used was novel, several procedural optimizations were required. Specifically, the ultracentrifugation gradient to be used as a partitioning method during the selection rounds was determined, DNA library amplification by polymerase chain reaction was optimized, polyacrylamide gel electrophoresis preparation and visualization protocols for round-to-round characterization were determined, and transmission electron microscopy methods for visualizing oligomerization inhibition were utilized.

During this optimization process, polyacrylamide gel electrophoresis using a protein ladder control was used to determine which fractions likely contained either alpha-synuclein monomer, tetramer or aggregate. By knowing the theoretical mass of these alpha-synuclein forms and the approximate mass of the DNA selection template, the fraction in which free alpha-synuclein monomer and unbound DNA, the fraction in which alpha-synuclein monomer bound to DNA, and the fraction in which alpha-synuclein aggregate bound to DNA were localized and determined. During the selection process, the general trend in fluorescence suggested that the majority of the DNA library was binding to smaller oligomer and monomer protein species, in contrast to the fluorescence trend observed for the M5-15 aptamer which suggested that the M5-15 aptamer bound preferentially to oligomers.

Upon examination of the images obtained by transmission electron microscopy (FIG. 1), the result was clear. The selection library had an inhibitory effect on the aggregation of alpha-synuclein protein (compare control and library in FIG. 1). This becomes obvious when comparing the size and morphology of protein imaged in fractions 14 and 20. Compared to the control images where alpha-synuclein aggregation was allowed to occur in the absence of inhibitors, the selection library (FIG. 1: Library) yielded much smaller protein structures. Therefore, we were able to select novel inhibitory aptamers and after 5 rounds of selection, the DNA library was analyzed by high-throughput sequencing (HTS).

Figure 2:
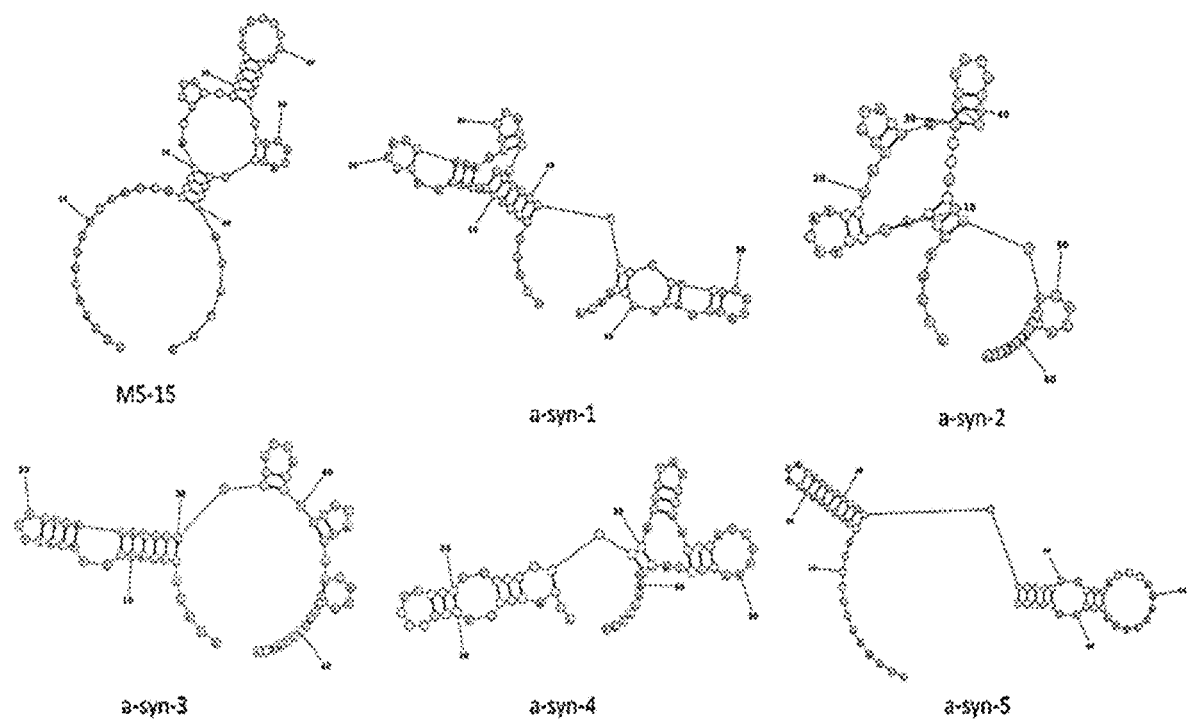
FIG. 2: RNAStructure was used to predict the secondary structure of the α-syn aptamers and the M5-15 control (Tsukakoshi, K.; Harada, R.; Sode, K.; Ikebukuro, K. Biotechnol. Lett. 2010, 32 (5), 643-648.).

The in vitro characterization of the aptamer candidates identified by the analysis of HTS data began with a structural analysis. The secondary structure of the aptamers was predicted using RNAstructure (FIG. 2). Similarly to the M5-15 aptamer, all of the predicted secondary structures consisted of multiple stem loop motifs. The structural complexity of the predicted secondary structures varied from a more common 2-way junction to a much less common 4-way junction.

To determine the tendency of each aptamer candidate to prevent alpha-synuclein aggregation, the average particle size imaged using transmission electron microscopy was determined. The average size for each of the aptamer candidates were as follows; M5-15 (266±135 nm), a-syn-1 (87±34 nm), a-syn-2 (176±128 nm), a-syn-3 (94±67 nm), a-syn-4 (156±68 nm) and a-syn-5 (98±38 nm). The average particle size of the a-syn control was 242±220 nm. While the variance was high, these data considered with the HTS data, suggested that the a-syn-1 aptamer binds specifically to alpha-synuclein monomer and is the most effective as an aggregation inhibitor out of the 5 aptamer candidates. Therefore, a-syn-1 was investigated further in vitro and was chosen as the first aptamer candidate to be investigated in vivo.

For the in vitro phase, a-syn-1 and alpha-synuclein monomer were incubated in a 1:1 ratio in phosphate buffered saline at physiological pH. Alpha-synuclein alone and alpha-synuclein in a 1:1 ratio with M5-15 were also prepared as experimental controls. Small aliquots of each reaction were prepared for transmission electron microscopy at the following time points: 4 days, 8 days, 10 days and 25 days. On day 4, the control and M5-15 images revealed the formation of larger protein aggregates than were observed in the a-syn-1 and alpha-synuclein monomer reaction. This trend continued on days 8 and 10, where generally larger aggregates were observed in the alpha-synuclein control and the M5-15 aptamer and alpha-synuclein reaction. After 25 days, much larger protein aggregates were observed in the alpha-synuclein control and the M5-15 aptamer and alpha-synuclein reaction compared to those observed in the a-syn-1 aptamer candidate and alpha-synuclein reaction. These results demonstrated that a-syn-1 was able to inhibit in vitro aggregation of alpha-synuclein over 25 days and was more effective than the M5-15 aptamer.

Figure 3:
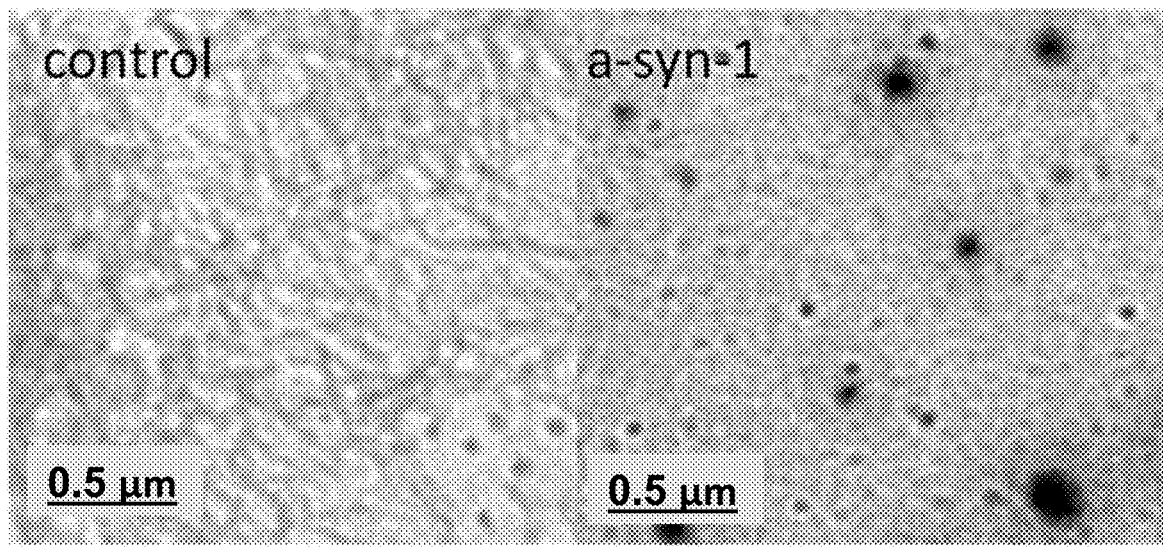
FIG. 3: Transmission electron microscopy images of pre-formed fibrils generated from alpha-synuclein monomer (control) in comparison to the minimal aggregation observed in the presence of the inhibitory aptamer (α-syn-1).

In another, in vitro characterization phase, the ability of a-syn-1 to interfere with the formation of alpha-synuclein fibrils was assessed. As shown in FIG. 3, there was a clear difference in the protein morphology of images from the control reaction compared to images from the a-syn-1 reaction. In the absence of the inhibitory a-syn-1 aptamer, fibrils were observed (control). In the presence of the a-syn-1 aptamer candidate, much smaller, spherical to amorphous morphology was observed (a-syn-1; FIG. 3). Notably, no fibrils were observed in the presence of a-syn-1. These data, along with the in vitro aggregation experiment over time, showed that the newly developed a-syn-1 aptamer not only inhibited alpha-synuclein aggregation but also the formation of fibrils in vitro.

In order to assess the inhibition of oligomers and fibril formation in vivo, the a-syn-1 aptamer was packaged into a targeting liposome vehicle for transport across the blood-brain barrier. To this end, small, unilamellar liposomes were prepared. Briefly, the phospholipids were dissolved in chloroform in a round bottom flask then the solution was dried under argon to produce a lipid film. Once the film was hydrated with aqueous buffer, the solution was sonicated and liposomes with a heterodisperse distribution were produced. The a-syn-1 aptamer was loaded into the liposome by adding ethanol to the flask and subjecting the liposomes to multiple freeze-thaw cycles. Once the a-syn-1 aptamer was encapsulated, the liposome solution was extruded through a 100 nm polycarbonate membrane to remove larger vesicles and produce a more monodisperse liposome size distribution. Finally, the surface of the liposome was modified with an aptamer that binds to the transferrin receptor. The transferrin receptor aptamer bound specifically to the membrane bound transferrin receptor, allowing the transferrin receptor aptamer to act as a targeting moiety and induce selective transport of the a-syn-1 aptamer loaded liposomes across the blood brain barrier. Polyacrylamide gel electrophoresis and UV-visible spectroscopy were used to monitor the liposome synthesis. Gel electrophoresis was used to assess loading of the a-syn-1 aptamer into the liposome and UV-Visible spectroscopy was used to confirm the conjugation of the transferrin aptamer to the surface of the liposome.

Figures 4A, 4B, 4C:
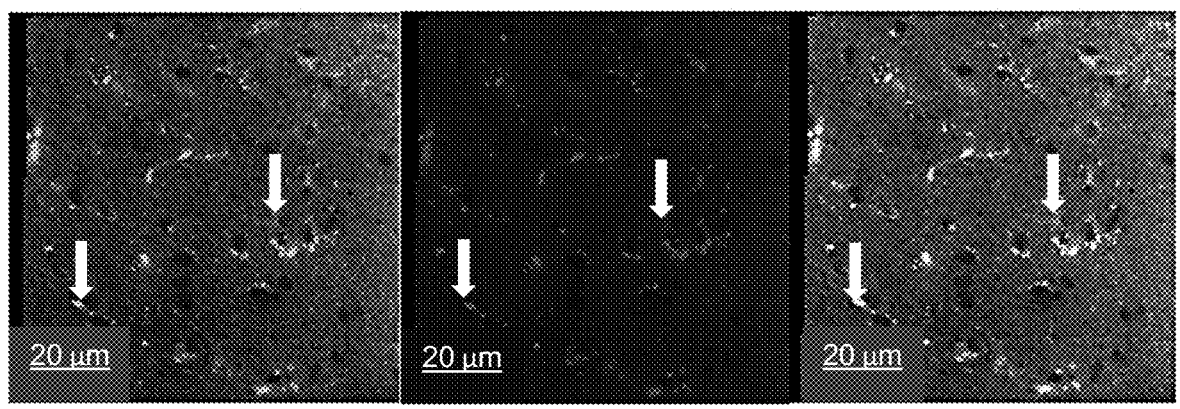
FIGS. 4A-AC: Fluorescence microscopy was used to image the distribution of α-syn-1 aptamer in brain tissue. Left (FIG. 4A): anti-alpha-synuclein (phospho S129) antibody. Middle (FIG. 4B): fluorescently-(Cy3.5) labelled aptamer, delivered by targeting liposome. Right (FIG. 4C): Image overlay showing extensive co-localization. Arrows point to cells with overlapping staining.

The a-syn-1 aptamer loaded liposomes were assessed in an acute study as well as a longitudinal study. In the acute study, transgenic mice were injected with 0.1 mL of the a-syn-1 aptamer loaded liposome. After 30 minutes, the animals were euthanized and the brains were removed to investigate the distribution of the a-syn-1 aptamer in brain tissue. The distribution of aptamer was assessed by fluorescence microscopy (FIGS. 4A-4C). Co-localization of the green fluorescence from the secondary antibody recognizing the phosphor-specific anti-alpha-synuclein antibody and the red fluorescence from the Cy3.5-labeled a-syn-1 aptamer was revealed by fluorescence microscopy. This study confirmed the delivery of the aptamer to the brain and that the a-syn-1 aptamer binds to alpha-synuclein in vivo. This preliminary evidence suggests that the a-syn-1 aptamer could be used as a fluorescence imaging probe. This would provide a more cost effective alternative to the traditional antibody method. Additionally, using an aptamer based fluorescence imaging probe only requires one component, unlike antibodies that often require secondary antibodies.

In the longitudinal study, male transgenic mice (mice express the human A53T variant a-synuclein under the direction of a mouse prion protein promoter (Tg(Prnp-SNCA*A53T)83Vle; n=2) received a 0.1 mL injection of the a-syn-1 aptamer loaded liposomes for three consecutive days, for three months in a row (totaling nine injections). Following the last of the nine injections, the animals were euthanized and brain tissue was collected to examine the inhibitory effect of the a-syn-1 aptamer on alpha-synuclein aggregation in vivo. Immunohistochemical staining for phosphorylated alpha-synuclein in 6-month old male transgenic mice and age-matched controls revealed a significant reduction on the number of alpha-synuclein positive cells in the aptamer-injected mice (* represents p<0.05) in the motor cortex. The in vivo work suggests that the a-syn-1 packaged into a liposome coated with transferrin receptor aptamers can 1) cross the blood brain barrier and bind to alpha-synuclein in the brain (acute study results) and 2) with repeated injections, a-syn-1 has an inhibitory effect on alpha-synuclein aggregation in the brain (repeated study results).

Figure 5:
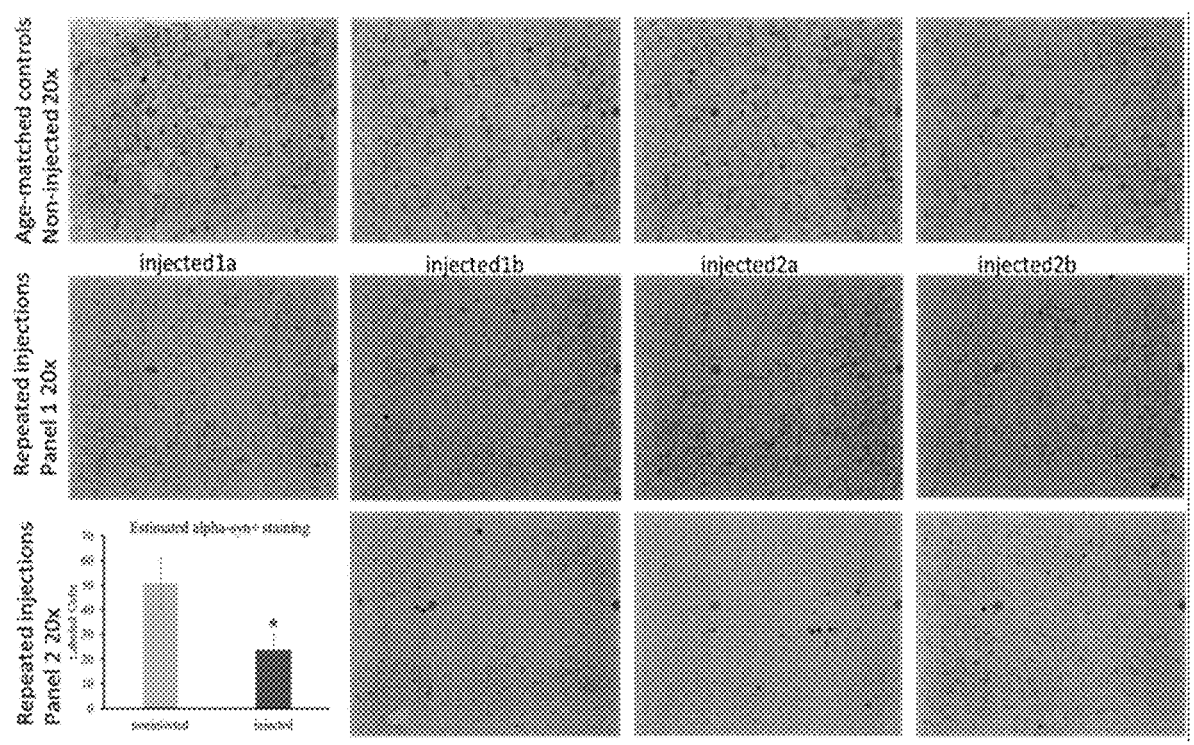
FIG. 5: Top panels show immunihistochemical staining for phosphorylated alpha-synuclein in 6-month old male transgenic mice (Mice express the human A53T variant α-synuclein under the direction of a mouse prion protein promoter (Tg(Prnp-SNCA*A53T)83Vle); age-matched controls; mouse 1 and mouse 2 are different Tg mice and a and b show slightly different regions of staining) in the motor cortex. Bottom panels show immunohistochemical staining for phosphorylated alpha-synuclein in 6-month old transgenic mice that received nine (9) 0.1 mL Asyn-1 aptamer injections (3 consecutive days of treatment per month for 3 months) in the motor cortex (mouse 1 and 2 represent different mice and a and b represent different regions within the motor cortex). Quantification in lower left panel shows estimated number of alpha-synuclein positive cells in the noninjected controls (images from top panel) and aptamer-injected mice (images from panel 1—middle row). T-test applied to the data revealed a significant reduction on the number of alpha-synuclein positive cells in the aptamer-injected mice (* represents p<0.05).

FIG. 5 Top panels show immunohistochemical staining for phosphorylated alpha-synuclein in 6-month old male transgenic mice (Mice express the human A53T variant a-synuclein under the direction of a mouse prion protein promoter (Tg(Prnp-SNCA*A53T)83Vle); age-matched controls; mouse 1 and mouse 2 are different Tg mice and a and b show slightly different regions of staining) in the motor cortex. Bottom panels show immunohistochemical staining for phosphorylated alpha-synuclein in 6-month old transgenic mice that received nine (9) 0.1 mL Asyn-1 aptamer injections (3 consecutive days of treatment per month for 3 months) in the motor cortex (mouse 1 and 2 represent different mice and a and b represent different regions within the motor cortex). Quantification in lower left panel shows estimated number of alpha-synuclein positive cells in the noninjected controls (images from top panel) and aptamer-injected mice (images from panel 1—middle row). T-test applied to the data revealed a significant reduction on the number of alpha-synuclein positive cells in the aptamer-injected mice (* represents p<0.05).

Figure 6:
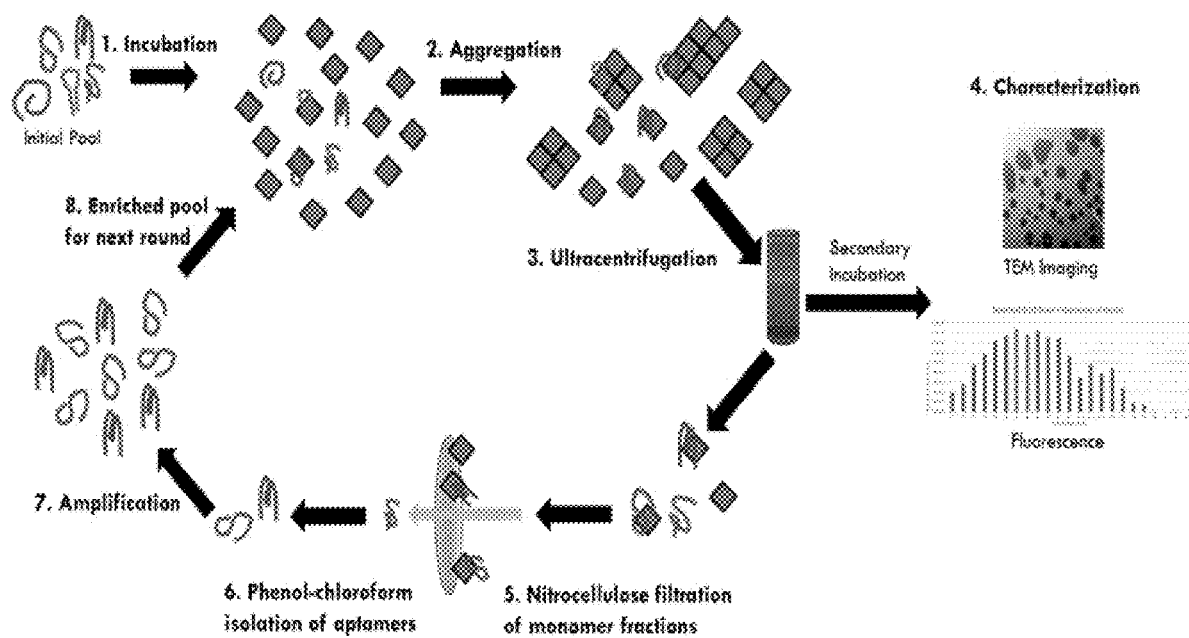
FIG. 6 depicts selection of aptamers that inhibit aggregation of alpha-synuclein monomer by SELEX. In each round of selection, a random DNA oligonucleotide library was incubated with the monomer protein (1). Aggregation was induced (2) and aptamers that bound specifically to monomer protein were isolated by ultracentrifugation (3). The fractions that contained aptamers that were able to prevent aggregation of the monomer protein were identified by transmission electron microscopy and fluorescence spectroscopy (4). Those fractions of interest were subjected to a nitrocellulose filtration (5) to remove unbound DNA, then the binding DNA were recovered by phenol-chloroform extraction (6). Following amplification of the extracted DNA, the enriched DNA library (8) was subjected to another round of selection.

FIG. 6 depicts selection of aptamers that inhibit aggregation of alpha-synuclein monomer by SELEX. In each round of selection, a random DNA oligonucleotide library was incubated with the monomer protein (1). Aggregation was induced (2) and aptamers that bound specifically to monomer protein were isolated by ultracentrifugation (3). The fractions that contained aptamers that were able to prevent aggregation of the monomer protein were identified by transmission electron microscopy and fluorescence spectroscopy (4). Those fractions of interest were subjected to a nitrocellulose filtration (5) to remove unbound DNA, then the binding DNA were recovered by phenol-chloroform extraction (6). Following amplification of the extracted DNA, the enriched DNA library (8) was subjected to another round of selection.

Figure 7:
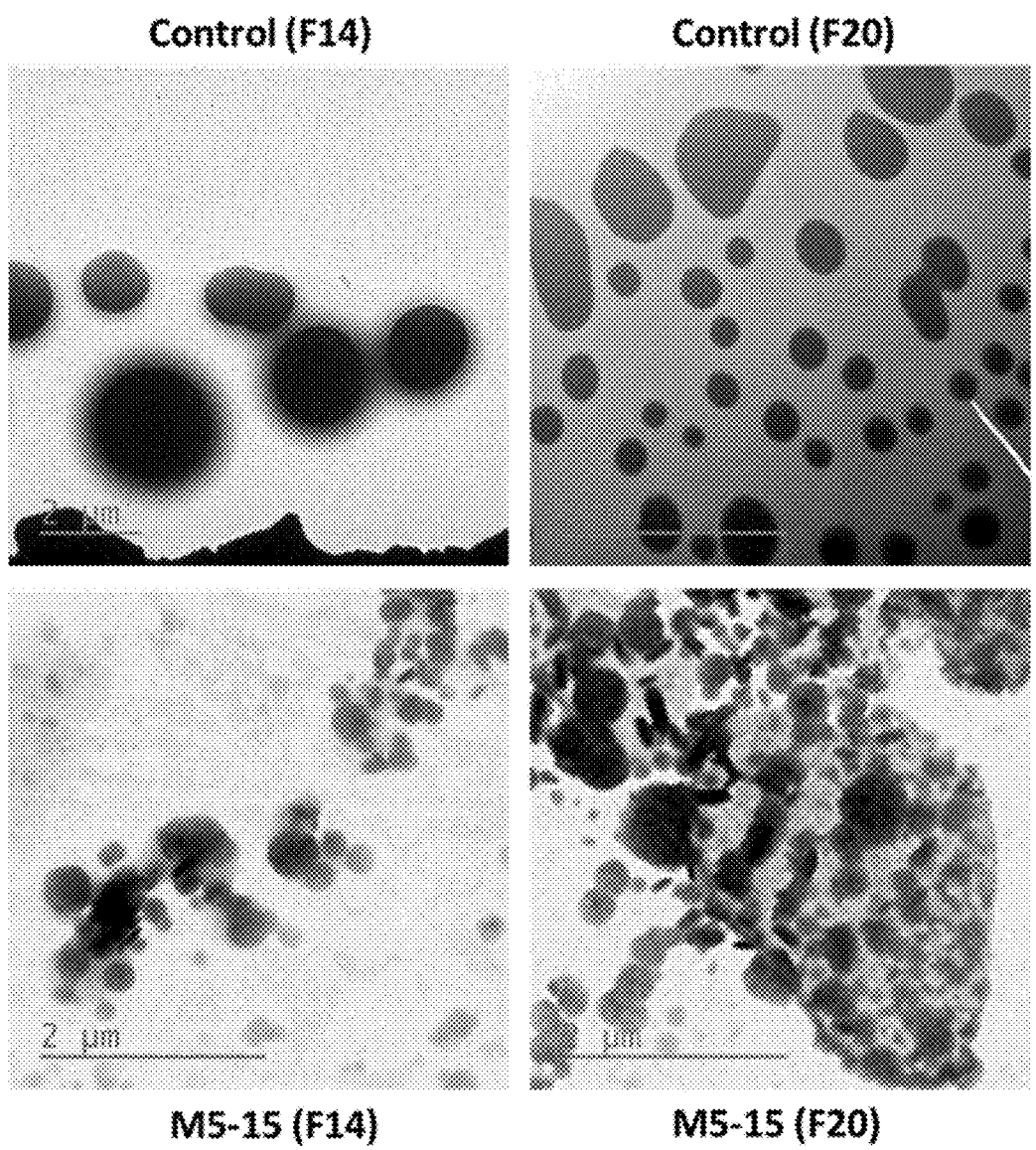
FIG. 7: The inhibitory effect of a previously selected alpha-synuclein binding aptamer, M5-15, on preventing aggregation was examined under the conditions of the SELEX experiment—Analysis of alpha-synuclein protein morphology by transmission electron microscopy (TEM) in the absence (control) and presence of the M5-15 aptamer. The number in brackets represents the fraction, post ultracentrifugation of which the protein morphology was examined. Representative images are shown.

FIG. 7: Depicts inhibitory effect of a previously selected alpha synuclein binding aptamer, M5-15, on preventing aggregation examined under conditions of the SELEX experiments. FIG. 7 shows analysis of alpha-synuclein protein morphology by transmission electron microscopy (TEM) in the absence (control) and presence of the M5-15 aptamer. The number in brackets represents the fraction, post ultracentrifugation of which the protein morphology was examined. Representative images are shown.

Figure 8:
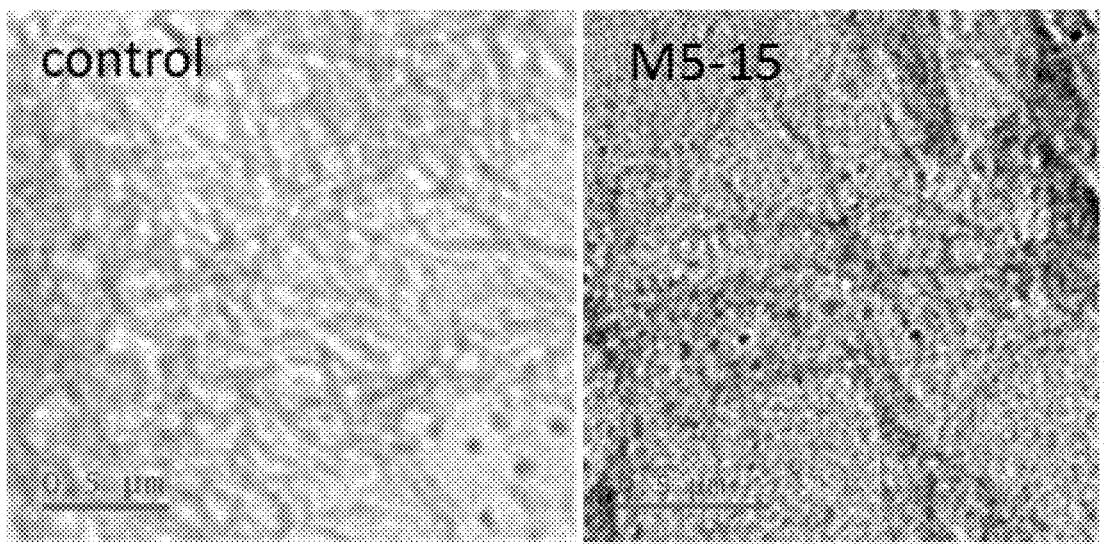
FIG. 8: The inhibitory effect of a previously selected alpha-synuclein binding aptamer, M5-15, on preventing aggregation was examined following the protocol detailed by the MJFF for the formation of pre-formed fibrils from monomer alpha-synuclein protein. Transmission electron microscopy images of pre-formed fibrils generated from alpha-synuclein monomer (control) in comparison to those observed in the presence of the inhibitory aptamer (M5-15).

FIG. 8: Depicts the inhibitory effect of a previously selected alpha-synuclein binding aptamer, M5-15, on preventing aggregation was examined following the protocol detailed by the MJFF for the formation of pre-formed fibrils from monomer alpha-synuclein protein. FIG. 8 shows Transmission electron microscopy images of pre-formed fibrils generated from alpha-synuclein monomer (control) in comparison to those observed in the presence of the inhibitory aptamer (M5-15).

Table 6 shows Alpha-synuclein binding aptamer candidates identified through the analysis of high-throughput sequencing data using AptaTools

TABLE 6

| Aptamer Candidate | Sequence (5'→3') | Enrichment In the Final Round Positive Fraction | Final Round Positive Pool Fraction Trend | Final Round Selectivity |
|---|---|---|---|---|
| a-syn-1 (1LBwAAjJ) (SEQ ID NO: 1) | ATAGTCCCATCA TTCATTGTAAGG AAACGCTACGGC GTGGGTACGGCA AGATATTAGCAA GTGTCA | This sequence showed the highest enrichment value | This sequence had the second highest representation | This sequence was only observed in the monomer binding fractions (positive and weakly binding negative) |
| a-syn-2 (1LBiGJFJC) (SEQ ID NO: 2) | ATAGTCCCATCA TTCATTGTATGGT ACGGCGCGGTGC CGGGTGCGGGGA GATATTAGCAAG TGTCA | This sequence had the second highest enrichment value | This sequence had the highest representation | This sequence was observed in the monomer binding fraction (positive) and the non-specific (negative) fraction |
| a-syn-3 (GdJUhe) (SEQ ID NO: 3) | ATAGTCCCATCA TTCATTGTATGA GATGGGGTGGTG ACGTCAGCATGG AGATATTAGCAA GTGTCA | This sequence had the third highest enrichment value | This sequence was equally represented compared to a-syn-1 | This sequence was observed in the monomer fraction, but also in the aggregate (counter) fractions and both negative fractions |
| a-syn-4 (LTMul1) (SEQ ID NO: 4) | ATAGTCCCATCA TTCATTGAACGG AATGGCGCGGTG ACCGGATAGTGT AGATATTAGCAA GTGTCA | This sequence had the lowest enrichment value | This sequence had the third highest representation | This sequence was observed in monomer fractions (positive, and both negative) |
| a-syn-5 (JueRc) (SEQ ID NO: 5) | ATAGTCCCATCA TTCATTGTATGAT ACAGTGAGGTGC CAGATGCATGCA GATATTAGCAAG TGTCA | This sequence showed the fourth highest enrichment value | This sequence had the lowest representation | This sequence was present in both monomer fractions (positive, and both negative) as well as the aggregate (counter) fraction |

Figure 9:
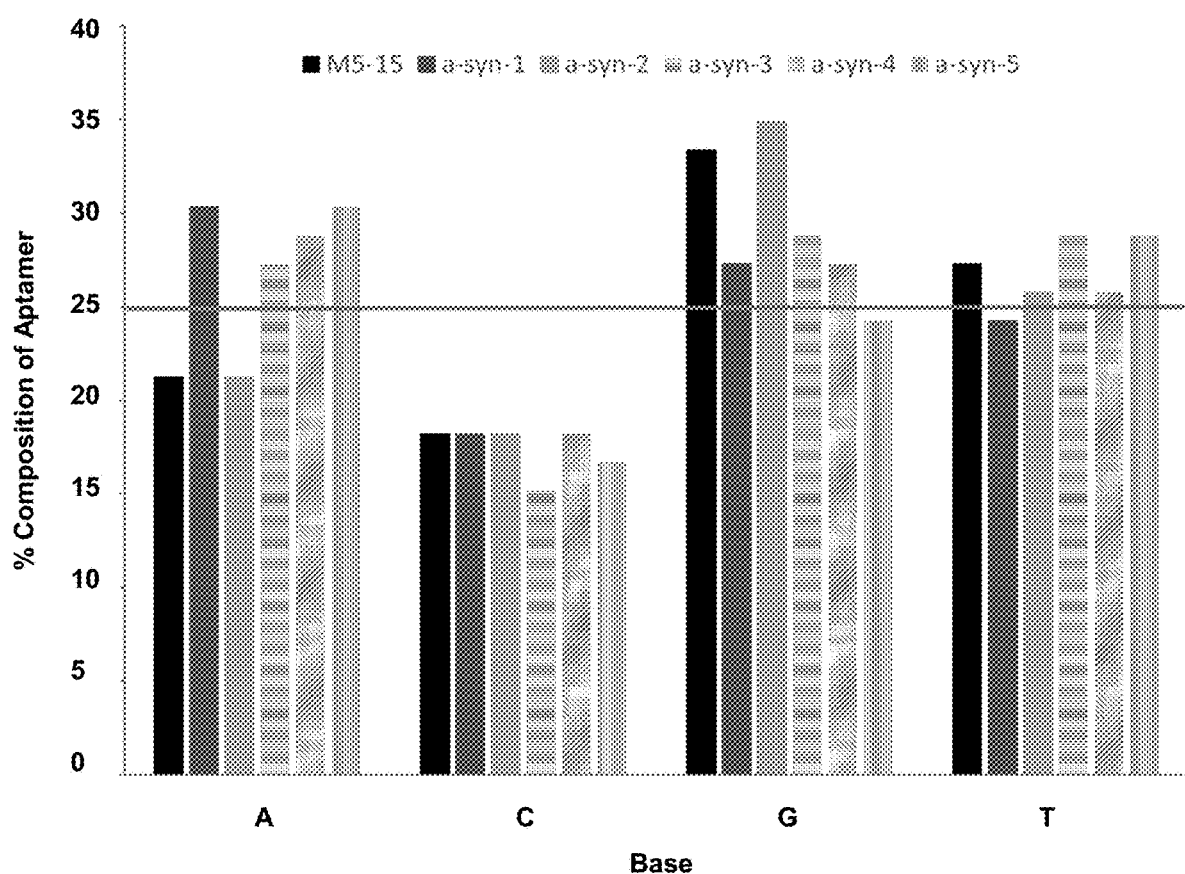
FIG. 9: Percent base composition of the M5-15 aptamer and the aptamer candidates. The grey line represents the expected base composition of a completely random DNA oligonucleotide.

FIG. 9 depicts Percent base composition of the M5-15 aptamer and the aptamer candidates. The grey line represents the expected base composition of a completely random DNA oligonucleotide.

Table 7: Predicted G-quadruplex regions in M5-15 and the aptamer candidates.

TABLE 7

| Aptamer Candidate | Position | Length | QGRS | G-Score | Number of G-Quad predicted | |
|---|---|---|---|---|---|---|
| M5-15 | 23 | 18 | GGTACGGCGCGGTGGCGG | 20 | 25 | SEQ ID NO: 22 |
| a-syn-1 | 34 | 13 | GGGGTGGGTACGG | 18 | 11 | SEQ ID NO: 23 |
| a-syn-2 | 23 | 18 | GGTACGGCGCGGTGGCGG | 20 | 71 | SEQ ID NO: 24 |
| a-syn-3 | 28 | 21 | GGGGTGGTGACGTCAGCATGG | 9 | 1 | SEQ ID NO: 25 |
| a-syn-4 | 23 | 19 | GGAATGGCGCGGTGACCGG | 19 | 1 | SEQ ID NO: 26 |
| a-syn-5 | — | — | — | — | 0 | |

FIGS. 10A-10B: The secondary structure of the a-syn aptamer candidates was examined by thermal denaturation. Thermal denaturation (tracked by UV-Vis spectroscopy) was used to evaluate the M5-15 aptamer and aptamer candidates for the presence of G-quadruplex secondary structure. The absorbance of the aptamer in the presence of 140 mM NaCl at 295 nm was monitored over the temperature gradient of 20° C.-80° C. Representative traces are shown for a-syn-1 and a-syn-2. M5-15 showed hypochromicity at 295 nm (data not shown) and the remaining aptamer candidates showed hyperchromicity at 295 nm (data not shown).

Figure 11:
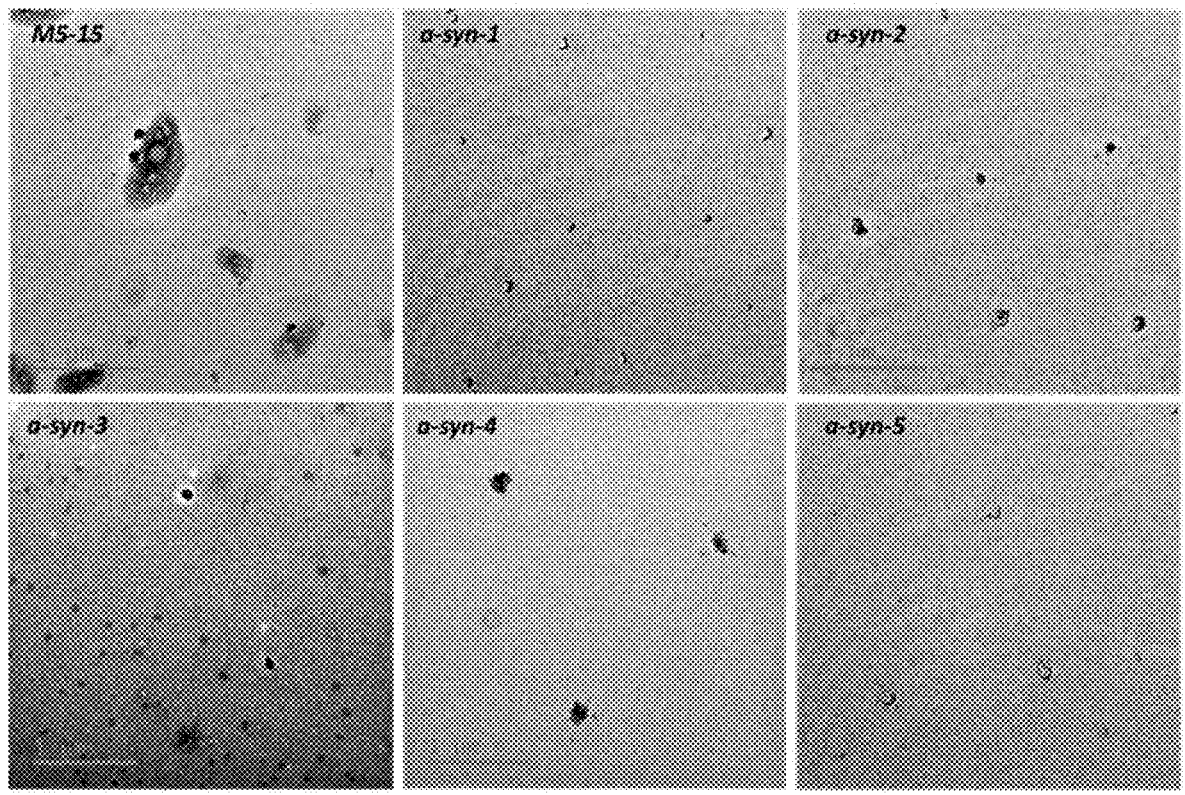
FIG. 11: The inhibitory effect of each aptamer candidate was examined under the selection conditions. Aptamer candidates were screened for their ability to prevent alpha-synuclein protein aggregation in vitro using transmission electron microscopy. Representative images from Fraction 10 are shown.

FIG. 11: The inhibitory effect of each aptamer candidate was examined under the selection conditions. Aptamer candidates were screened for their ability to prevent alpha-synuclein protein aggregation in vitro using transmission electron microscopy. Representative images from Fraction 10 are shown.

Figure 12:
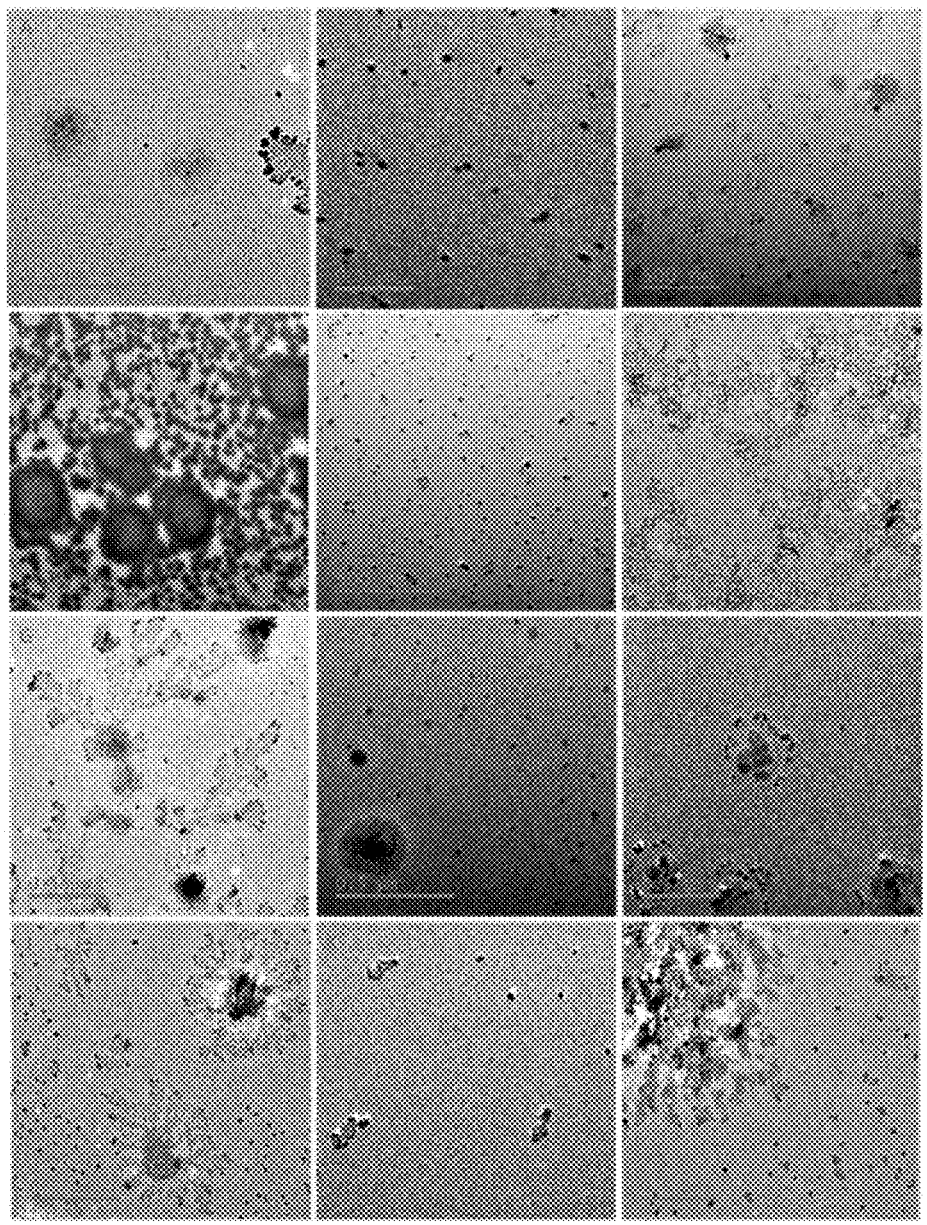
FIG. 12: Longitudinal investigation of the inhibitory effect of aptamer α-syn-1 on protein aggregation under selection conditions. Longitudinal investigation of alpha-synuclein aggregation inhibition by α-syn-1 by transmission electron microscopy. TEM images were obtained on day 4 (A, B, C), day 8 (D, E, F), day 10 (G, H, 1), and day 25 (J, K, L). Images A, D, G and J were controls (alpha-synuclein alone), B, E, H and K were alpha-synuclein+aptamer candidate α-syn-1, and images C, F, I and L were alpha-synuclein+M5-15 aptamer.

FIG. 12: Longitudinal investigation of the inhibitory effect of aptamer a-syn-1 on protein aggregation under selection conditions. Longitudinal investigation of alpha-synuclein aggregation inhibition by a-syn-1 by transmission electron microscopy. TEM images were obtained on day 4 (A, B, C), day 8 (D, E, F), day 10 (G, H, 1), and day 25 (J, K, L). Images A, D, G and J were controls (alpha-synuclein alone), B, E, H and K were alpha-synuclein+aptamer candidate a-syn-1, and images C, F, I and L were alpha-synuclein+M5-15 aptamer.

Figure 13:
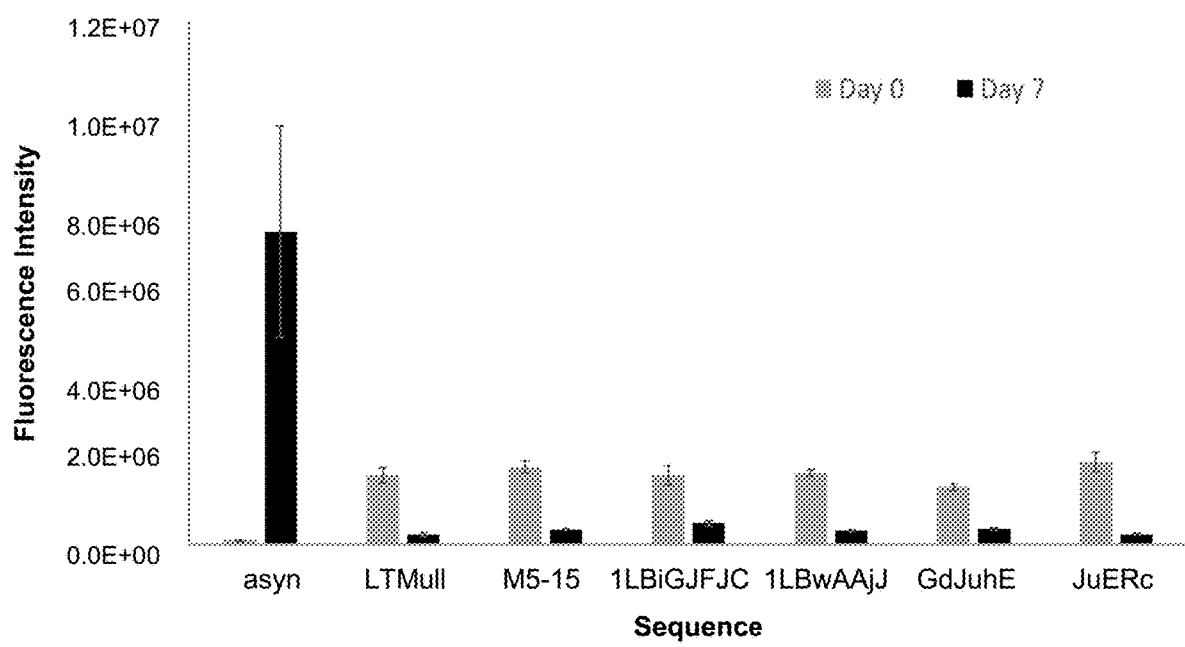
FIG. 13: Fibrillization was confirmed using the Thioflavin T assay as described in the MJFF protocol for the generation of pre-formed fibrils from alpha-synuclein monomer (Volpicelli-Daley, L. A. et al. Addition of exogenous α-synuclein pre-formed fibrils to primary neuronal cultures to seed recruitment of endogenous α-synuclein to Lewy body and Lewy neurite-like aggregates. Nat. Protoc. 9(9):2135-46 (2014).). The Thioflavin T assay was used to confirm the formation of alpha-synuclein fibrils after 7 days.

FIG. 13: Fibrillization was confirmed using the Thioflavin T assay as described in the MJFF protocol for the generation of pre-formed fibrils from alpha-synuclein monomer (Volpicelli-Daley, L. A. et al. Addition of exogenous α-synuclein pre-formed fibrils to primary neuronal cultures to seed recruitment of endogenous α-synuclein to Lewy body and Lewy neurite-like aggregates. Nat. Protoc. 9(9):2135-46 (2014).) The Thioflavin T assay was used to confirm the formation of alpha-synuclein fibrils after 7 days. An increase in fluorescence intensity on day 7 compared to day 0 was indicative of fibril formation.

Figure 14:
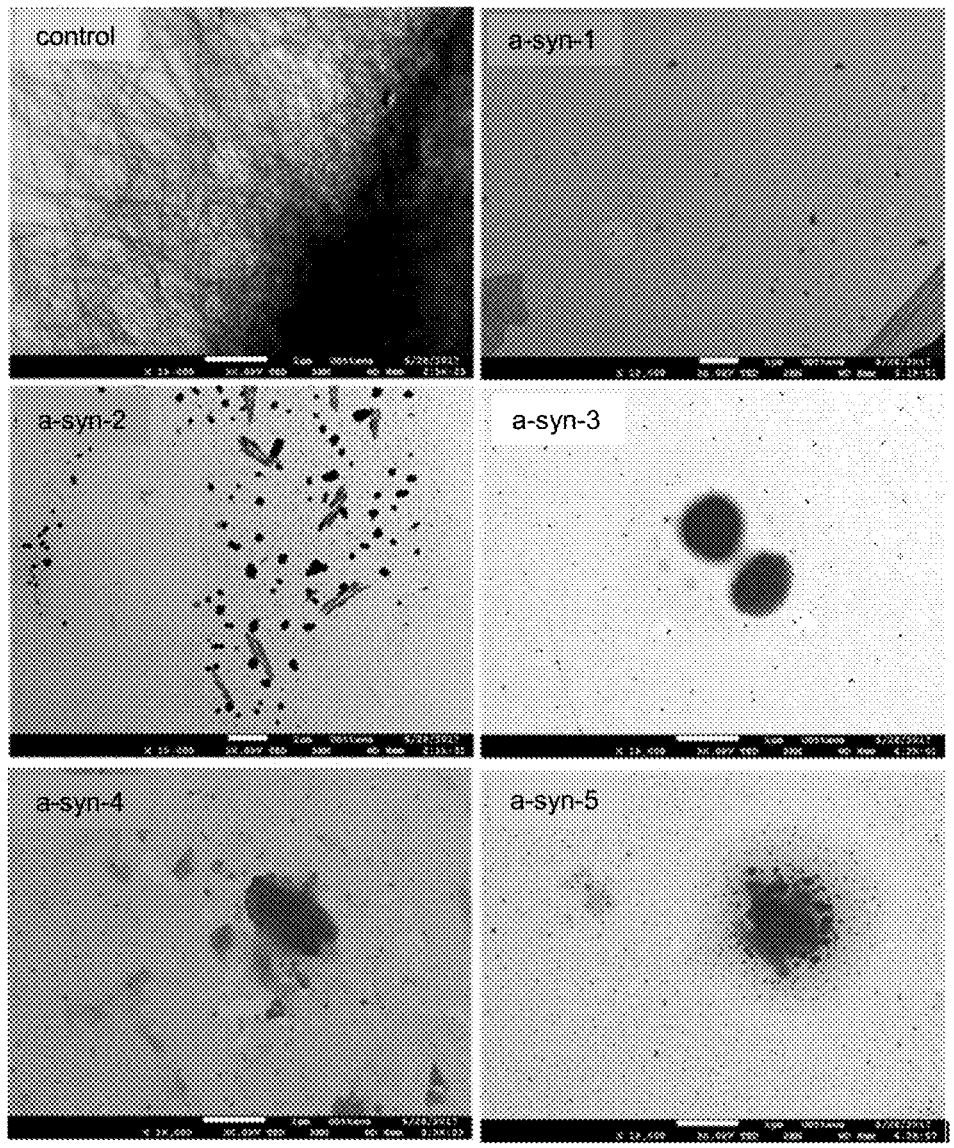
FIG. 14: Electron microscopy was used to investigate the inhibitory effect of the aptamer candidates following the MJFF protocol for generation of pre-formed fibrils from alpha-synuclein monomer. Scanning Electron Microscopy (SEM) was used to image the inhibitory effect of the aptamer candidates on alpha-synuclein fibril formation after 7 days. Representative images are shown.

FIG. 14: Electron microscopy was used to investigate the inhibitory effect of the aptamer candidates following the MJFF protocol for generation of pre-formed fibrils from alpha-synuclein monomer. Scanning Electron Microscopy (SEM) was used to image the inhibitory effect of the aptamer candidates on alpha-synuclein fibril formation after 7 days. Representative images are shown.

FIGS. 15A-15B: The DNA footprint (left) (FIG. 15A) produced by the interaction of DNase I with the a-syn-1 aptamer-alpha synuclein monomer binding complex is shown. Lanes contained 10 μM DNA and alpha synuclein at the following concentrations: 0 μM (C), 15 μM (1), 1.5 μM (2), 0.3 μM (3), 0.06 μM (4), 0.012 μM (5) and 0.0024 μM (6). The changes in the relative integrated density value (IDV) of three bands (highlighted by top, middle, and bottom boxes) were used to estimate the apparent KD of the aptamer-target interaction. (FIG. 15B) A sample binding isotherm, generated from the middle boxed data, is shown (right).

FIGS. 16A-16B: The DNA footprint (left)(FIG. 16A) produced by the interaction of DNase I with the positive control M5-15 aptamer-alpha synuclein monomer binding complex is shown. Lanes contained 10 μM DNA and alpha synuclein at the following concentrations: 0 μM (C), 17.5 μM (1), 1.75 μM (2), 0.175 μM (3), 0.0175 μM (4), and 0.00175 μM (5). The changes in the relative integrated density value (IDV) of three bands (top, middle, and bottom boxes) were used to estimate the apparent KD of the aptamer-target interaction. (FIG. 16B) A sample binding isotherm, generated from the middle boxed data, is shown (right).

Figure 17:
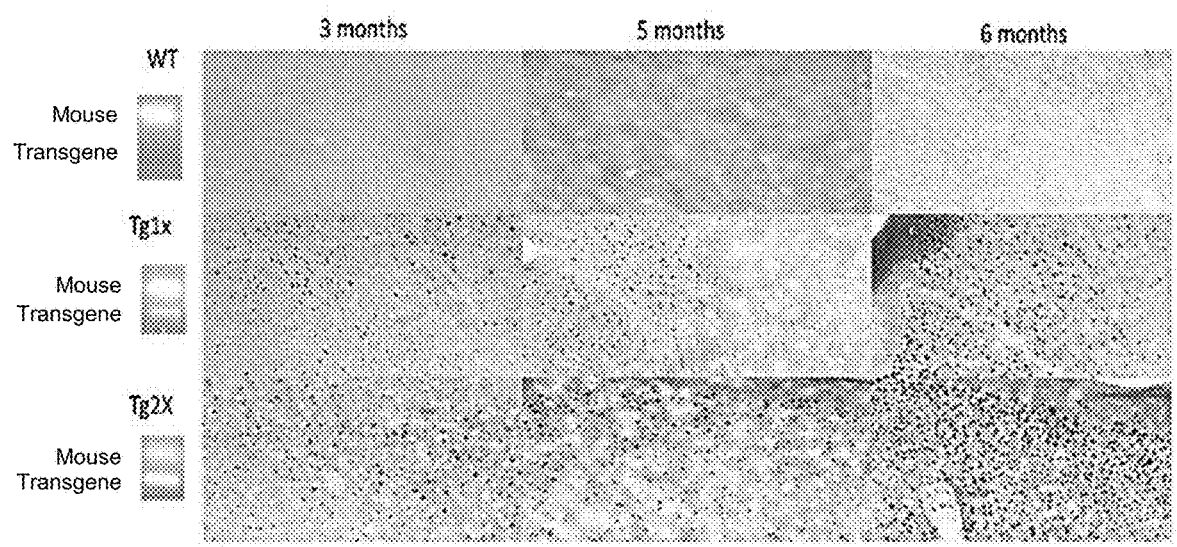
FIG. 17: Immunohistochemical analysis of phosphorylated (S129) human alpha-synuclein distribution in brain tissue obtained from wild type (WT), Tg1x and Tg2x aged 3 months, 5 months and 6 months. The transgene dosage was confirmed by PCR amplification and electrophoretic mobility. Representative images are shown. Male and female animals showed similar staining patterns.

FIG. 17: Immunohistochemical analysis of phosphorylated (S129) human alpha-synuclein distribution in brain tissue obtained from wild type (WT), Tg1x and Tg2x aged 3 months, 5 months and 6 months. The transgene dosage was confirmed by PCR amplification and electrophoretic mobility. Representative images are shown. Male and female animals showed similar staining patterns.

Figures 18A, 18B, 18C:
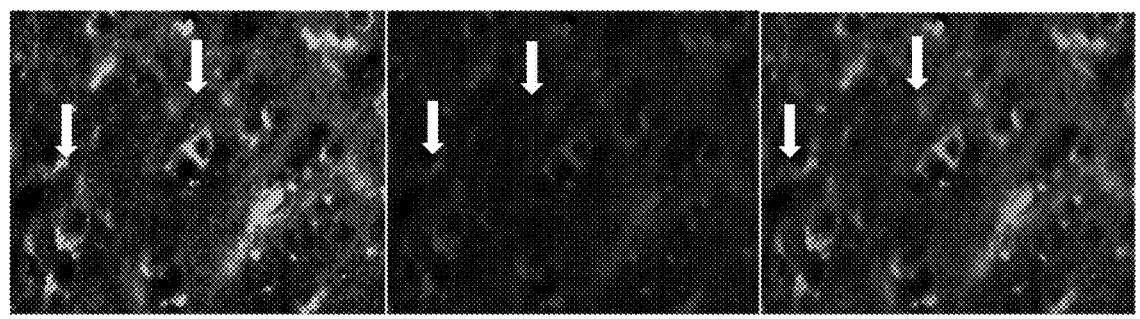
FIGS. 18A-18C Fluorescence microscopy images showing α-syn-1 binding after repeated injections of α-syn-TRAM. Fluorescence microscopy was used to image the distribution of α-syn-1 aptamer in brain tissue after repeated injection of α-syn-TRAM. α-syn-TRAM is Transferrin receptor Aptamer Modified (TRAM) liposomes containing the α-syn aptamer. Left (FIG. 18A): anti-alpha-synuclein (phospho S129) antibody. Middle (FIG. 18B): fluorescently-(Cy3.5) labelled aptamer. Right (FIG. 18C): Image overlay showing fluorescence co-localization.

FIGS. 18A-18C: Fluorescence microscopy images showing a-syn-1 binding after repeated injections of a-syn-TRAM. Fluorescence microscopy was used to image the distribution of a-syn-1 aptamer in brain tissue after repeated injection of a-syn-TRAM. a-syn-TRAM is Transferrin receptor Aptamer Modified (TRAM) liposomes containing the a-syn aptamer. Left (FIG. 18A): anti-alpha-synuclein (phospho S129) antibody. Middle (FIG. 18B): fluorescently-(Cy3.5) labelled aptamer. Right (FIG. 18C): Image overlay showing fluorescence co-localization.

FIGS. 19A-19B depict binding isotherms provided from 2bind for the FIG. 19A) a-syn-2, FIG. 19B) a-syn-3, The dissociation constant of a-syn-2 and a-syn-3 were calculated to be 285.5 nM±37.9 nM, 94.2 nM±2.8 nM, respectively. As shown here, the aptamers bind in the mid nanomolar range, as determined by microscale thermophoresis.

FIGS. 20A-20B depict slices from motor cortex (FIG. 20A) of A53T alpha-synuclein transgenic line M83 mouse model (12 months old) vs. age matched wild type mouse (FIG. 20B) both stained with 5'-fluorescein modified asyn1. These data demonstrate the ability of the aptamers to be used to label alpha synuclein in a tissue sample.

Figure 21:
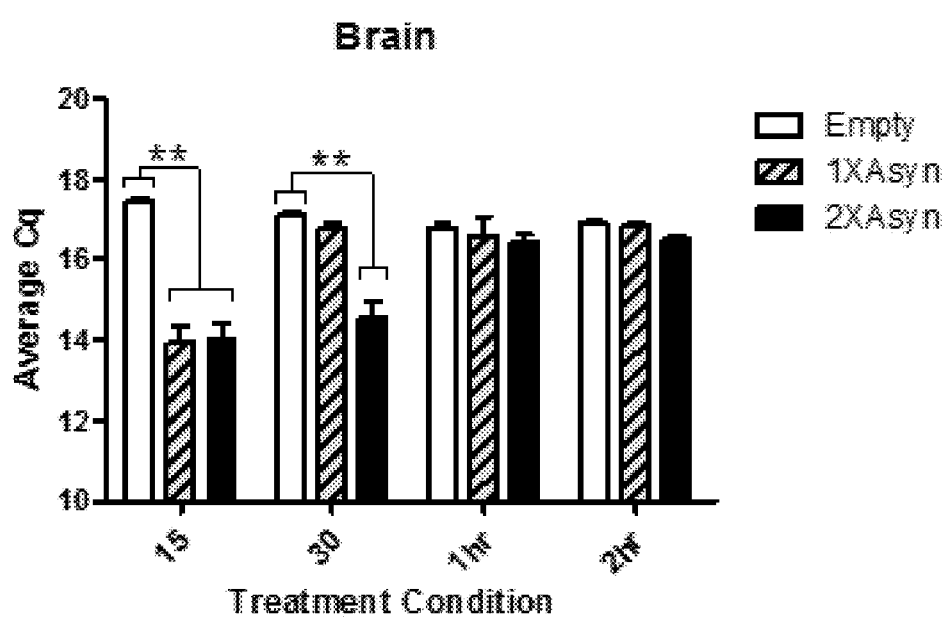
FIG. 21 depicts Average Cq values for qPCR experiments. In each case, 100 μL (1×) or 200 μL (2×) liposome solution (Calculated to be from $104 \times 10^{14}$ liposomes per 100 μL; an average of 10-20 aptamers per liposome) was injected i.p. Lower Cq values translate into greater numbers of aptamers detected. Aptamer could be detected in the cortex within 15 minutes at either dose and persisted longer at the 2× dose.

FIG. 21 depicts Average Cq values for qPCR experiments. In each case, 100 μL (1×) or 200 μL (2×) liposome solution (Calculated to be from $104 \times 10^{14}$ liposomes per 100 μL; an average of 10-20 aptamers per liposome) was injected i.p. Lower Cq values translate into greater numbers of aptamers detected. Aptamer could be detected in the cortex within 15 minutes at either dose and persisted longer at the 2× dose. These data demonstrate the ability of the aptamers to be used to label alpha synuclein in a tissue sample. These data show that the aptamer may be delivered and detected perfused brain tissue.

REFERENCES (1) Hickey, P.; Stacy, M. Drug Des. Devel. Ther. 2011, 5, 241-254.
(2) Angelova, P. R.; Abramov, A. Y. Biochem. Biophys. Res. Commun. 2017, 483 (4), 1110-1115.
(3) Rosborough, K.; Patel, N.; Kalia, L. V. Curr. Neurol. Neurosci. Rep. 2017, 17 (4), 31.
(4) Giasson, B. I.; Duda, J. E.; Quinn, S. M.; Zhang, B.; Trojanowski, J. Q.; Lee, V. M. Y. Neuron 2002, 34 (4), 521-533.
(5) Wong, Y. C.; Krainc, D. Nat. Med. 2017, 23 (2), 1-13.
(6) Singh, S. K.; Dutta, A.; Modi, G. Future Med. Chem. 2017, 9 (10), 1039-1053.
(7) Jpsko, H.; Lenkiewicz, A. M.; Adamczyk, A. Expert Opin. Ther. Pat. 2017, 27 (4), 427-438.
(8) Tuerk, C.; Gold, L. Science 1990, 249 (4968), 505-510.
(9) Ellington, A.; Szostak, J. Nature 1992, 355, 850-852.
(10) McKeague, M.; McConnell, E. M.; Cruz-Toledo, J.; Bernard, E. D.; Pach, A.; Mastronardi, E.; Zhang, X.; Beking, M.; Francis, T.; Giamberardino, A.; Cabecinha, A.; Ruscito, A.; Aranda-Rodriguez, R.; Dumontier, M.; DeRosa, M. C. J. Mol. Evol. 2015, 81 (5), 150-161.

(11) Ruigrok, V. J. B.; Levisson, M.; Eppink, M. H. M.; Smidt, H.; van der Oost, J. Biochem. J. 2011, 436, 1-13.
(12) Tolle, F.; Mayer, G. Chem. Sci. 2013, 4 (1), 60.
(13) Rusconi, C. P.; Scardino, E.; Layzer, J.; Pitoc, G. A.; Ortel, T. L.; Monroe, D.; Sullenger, B. a. Nature 2002, 419 (6902), 90-94.
(14) Takahashi, T.; Tada, K.; Mihara, H. Mol. Biosyst. 2009, 5 (9), 986-991.
(15) Chaudhary, R. K.; Patel, K. A.; Patel, M. K.; Joshi, R. H.; Roy, I. Mol. Ther. 2015, 23 (12), 1912-1926.
(16) Rhie, A.; Kirby, L.; Sayer, N.; Wellesley, R.; Disterer, P.; Sylvester, I.; Gill, A.; Hope, J.; James, W.; Tahiri-Alaoui, A. J. Biol. Chem. 2003, 278 (41), 39697-39705.
(17) Tsukakoshi, K.; Harada, R.; Sode, K.; Ikebukuro, K. Biotechnol. Lett. 2010, 32 (5), 643-648.
(18) Tsukakoshi, K.; Abe, K.; Sode, K.; Ikebukuro, K. Anal. Chem. 2012, 84 (13), 5542-5547.
(19) Hoinka, J.; Berezhnoy, A.; Dao, P.; Sauna, Z. E.; Gilboa, E.; Przytycka, T. M. Nucleic Acids Res. 2015, 43 (12), 5699-5707.
(20) Hoinka, J.; Berezhnoy, A.; Sauna, Z. E.; Gilboa, E.; Przytycka, T. M. Lect. Notes Comput. Sci. (including Subser. Lect. Notes Artif. Intell. Lect. Notes Bioinformatics) 2014, 8394 LNBI, 115-128.
(21) Müller, J.; Freitag, D.; Mayer, G.; Pötzsch, B. J. Thromb. Haemost. 2008, 6 (12), 2105-2112.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. An aptamer that binds to alpha-synuclein protein, comprising a nucleic acid having at least 90% sequence identity to a nucleic acid sequence selected from the group consisting of α-syn-1 (SEQ ID NO: 1), α-syn-3 (SEQ ID NO: 3), α-syn-4 (SEQ ID NO: 4), or α-syn-5 (SEQ ID NO: 5).

2. The aptamer of claim 1, wherein the nucleic acid has at least 95% sequence identity to a nucleic acid sequence selected from the group consisting of α-syn-1 (SEQ ID NO: 1), α-syn-3 (SEQ ID NO: 3), α-syn-4 (SEQ ID NO: 4), or α-syn-5 (SEQ ID NO: 5).

3. The aptamer of claim 1, wherein the nucleic acid is selected from the group consisting of α-syn-1 (SEQ ID NO: 1), α-syn-3 (SEQ ID NO: 3), α-syn-4 (SEQ ID NO: 4), or α-syn-5 (SEQ ID NO: 5).

4. The aptamer of claim 1, wherein the nucleic acid of the aptamer comprises a detectable label.

5. A kit comprising one or more of the aptamers of claim 1 and instructions for use thereof.

6. The kit of claim 5, wherein the nucleic acid of the aptamer is selected from the group consisting of α-syn-1 (SEQ ID NO: 1), α-syn-3 (SEQ ID NO: 3), α-syn-4 (SEQ ID NO: 4), or a-syn-5 (SEQ ID NO: 5).

7. The kit of claim 5, wherein the nucleic acid of the aptamer comprises a detectable label.

8. The kit of claim 5, further comprising a targeting moiety.

9. The kit of claim 5, further comprising a transferrin receptor aptamer.

10. The kit of claim 5, further comprising a neutral lipid, an anionic lipid, a cationic lipid, or a zwitterionic lipid.

11. A liposome comprising one or more lipids and at least one aptamer of claim 1.

12. The liposome of claim 11, further comprising a targeting moiety.

13. The liposome of claim 12, wherein said targeting moiety is a transferrin receptor aptamer.

14. A method of treating a subject having, or suspected of having, Parkinson's disease (PD), dementia with Lewy bodies (DLB), or multiple system atrophy (MSA), comprising: administering at least one aptamer of claim 1.

15. A method of treating a human subject having, or suspected of having, Parkinson's disease (PD), dementia with Lewy bodies (DLB), or multiple system atrophy (MSA), comprising: administering a pharmaceutical composition comprising at least one aptamer of claim 1, and a pharmaceutically acceptable carrier.

16. A method of treating a human subject having, or suspected of having, Parkinson's disease (PD), dementia with Lewy bodies (DLB), or multiple system atrophy (MSA), comprising: administering a liposome comprising at least one aptamer of claim 1, and optionally comprising a pharmaceutically acceptable carrier.

17. The method of claim 16, wherein said liposome further comprises a targeting moiety.

18. The method of claim 17, wherein said targeting moiety is a transferrin receptor aptamer.

* * * * *

SEQUENCE LISTING

```
<160> NUMBER OF SEQ ID NOS: 26

<210> SEQ ID NO 1
<211> LENGTH: 66
<212> TYPE: DNA
<213> ORGANISM: Artificial Sequence
<220> FEATURE:
<223> OTHER INFORMATION: a-syn-1 (1LBwAAjJ)

<400> SEQUENCE: 1
atagtcccat cattcattgt aaggaaacgc tacggggtgg gtacggcaag atattagcaa    60
gtgtca                                                              66

<210> SEQ ID NO 2
<211> LENGTH: 66
<212> TYPE: DNA
<213> ORGANISM: Artificial Sequence
<220> FEATURE:
<223> OTHER INFORMATION: a-syn-2 (1LBiGJFJC)

<400> SEQUENCE: 2
atagtcccat cattcattgt atggtacggc gcggtggcgg gtgcggggag atattagcaa    60
gtgtca                                                              66

<210> SEQ ID NO 3
<211> LENGTH: 66
<212> TYPE: DNA
<213> ORGANISM: Artificial Sequence
<220> FEATURE:
<223> OTHER INFORMATION: 3. a-syn-3 (GdJUhe)

<400> SEQUENCE: 3
atagtcccat cattcattgt atgagatggg gtggtgacgt cagcatggag atattagcaa    60
gtgtca                                                              66

<210> SEQ ID NO 4
<211> LENGTH: 66
<212> TYPE: DNA
<213> ORGANISM: Artificial Sequence
```

```
<220> FEATURE:
<223> OTHER INFORMATION: 4. a-syn-4 (LTMull)

<400> SEQUENCE: 4
atagtcccat cattcattga acggaatggc gcggtgaccg gatagtgtag atattagcaa      60
gtgtca                                                                66

<210> SEQ ID NO 5
<211> LENGTH: 66
<212> TYPE: DNA
<213> ORGANISM: Artificial Sequence
<220> FEATURE:
<223> OTHER INFORMATION: 5. a-syn-5 (JueRc)

<400> SEQUENCE: 5
atagtcccat cattcattgt atgatacagt gaggtggcag atgcatgcag atattagcaa      60
gtgtca                                                                66

<210> SEQ ID NO 6
<211> LENGTH: 66
<212> TYPE: DNA
<213> ORGANISM: Artificial Sequence
<220> FEATURE:
<223> OTHER INFORMATION: template
<220> FEATURE:
<221> NAME/KEY: misc_feature
<222> LOCATION: (19)..(48)
<223> OTHER INFORMATION: n is a, c, g, or t

<400> SEQUENCE: 6
atagtcccat cattcattnn nnnnnnnnnn nnnnnnnnnn nnnnnnnnag atattagcaa      60
gtgtca                                                                66

<210> SEQ ID NO 7
<211> LENGTH: 66
<212> TYPE: DNA
<213> ORGANISM: Artificial Sequence
<220> FEATURE:
<223> OTHER INFORMATION: M5-15 aptamer

<400> SEQUENCE: 7
atagtcccat cattcattgt atggtacggc gcggtggcgg gtgcgtggag atattagcaa      60
gtgtca                                                                66

<210> SEQ ID NO 8
<211> LENGTH: 18
<212> TYPE: DNA
<213> ORGANISM: Artificial Sequence
<220> FEATURE:
<223> OTHER INFORMATION: forward primer
<220> FEATURE:
<221> NAME/KEY: Fam
<222> LOCATION: (1)..(1)

<400> SEQUENCE: 8
atagtcccat cattcatt                                                   18

<210> SEQ ID NO 9
<211> LENGTH: 38
<212> TYPE: DNA
<213> ORGANISM: Artificial Sequence
<220> FEATURE:
<223> OTHER INFORMATION: reverse primer
<220> FEATURE:
<221> NAME/KEY: HEG
```

```
<222> LOCATION: (21)..(21)

<400> SEQUENCE: 9
aaaaaaaaaa aaaaaaaaaa tgacacttgc taatatct                                    38

<210> SEQ ID NO 10
<211> LENGTH: 76
<212> TYPE: DNA
<213> ORGANISM: Artificial Sequence
<220> FEATURE:
<223> OTHER INFORMATION: F1 primer

<400> SEQUENCE: 10
aatgatacgg cgaccaccga gatctacact ctttccctac acgacgctct tccgatctat            60
agtcccatca ttcatt                                                            76

<210> SEQ ID NO 11
<211> LENGTH: 77
<212> TYPE: DNA
<213> ORGANISM: Artificial Sequence
<220> FEATURE:
<223> OTHER INFORMATION: F2 Primer
<220> FEATURE:
<221> NAME/KEY: misc_feature
<222> LOCATION: (59)..(59)
<223> OTHER INFORMATION: n is a, c, g, or t

<400> SEQUENCE: 11
aatgatacgg cgaccaccga gatctacact ctttccctac acgacgctct tccgatctna            60
tagtcccatc attcatt                                                           77

<210> SEQ ID NO 12
<211> LENGTH: 78
<212> TYPE: DNA
<213> ORGANISM: Artificial Sequence
<220> FEATURE:
<223> OTHER INFORMATION: F3 Primer
<220> FEATURE:
<221> NAME/KEY: misc_feature
<222> LOCATION: (59)..(60)
<223> OTHER INFORMATION: n is a, c, g, or t

<400> SEQUENCE: 12
aatgatacgg cgaccaccga gatctacact ctttccctac acgacgctct tccgatctnn            60
atagtcccat cattcatt                                                          78

<210> SEQ ID NO 13
<211> LENGTH: 79
<212> TYPE: DNA
<213> ORGANISM: Artificial Sequence
<220> FEATURE:
<223> OTHER INFORMATION: F4 Primer
<220> FEATURE:
<221> NAME/KEY: misc_feature
<222> LOCATION: (59)..(61)
<223> OTHER INFORMATION: n is a, c, g, or t

<400> SEQUENCE: 13
aatgatacgg cgaccaccga gatctacact ctttccctac acgacgctct tccgatctnn            60
natagtccca tcattcatt                                                         79

<210> SEQ ID NO 14
<211> LENGTH: 82
<212> TYPE: DNA
<213> ORGANISM: Artificial Sequence
```

```
<220> FEATURE:
<223> OTHER INFORMATION: R1 Primer

<400> SEQUENCE: 14
caagcagaag acggcatacg agatcgtgat gtgactggag ttcagacgtg tgctcttccg    60
atcttgacac ttgctaatat ct                                             82

<210> SEQ ID NO 15
<211> LENGTH: 82
<212> TYPE: DNA
<213> ORGANISM: Artificial Sequence
<220> FEATURE:
<223> OTHER INFORMATION: R2 Primer

<400> SEQUENCE: 15
caagcagaag acggcatacg agatacatcg gtgactggag ttcagacgtg tgctcttccg    60
atcttgacac ttgctaatat ct                                             82

<210> SEQ ID NO 16
<211> LENGTH: 83
<212> TYPE: DNA
<213> ORGANISM: Artificial Sequence
<220> FEATURE:
<223> OTHER INFORMATION: R3 Primer
<220> FEATURE:
<221> NAME/KEY: misc_feature
<222> LOCATION: (65)..(65)
<223> OTHER INFORMATION: n is a, c, g, or t

<400> SEQUENCE: 16
caagcagaag acggcatacg agatgcctaa gtgactggag ttcagacgtg tgctcttccg    60
atctntgaca cttgctaata tct                                            83

<210> SEQ ID NO 17
<211> LENGTH: 83
<212> TYPE: DNA
<213> ORGANISM: Artificial Sequence
<220> FEATURE:
<223> OTHER INFORMATION: R4 Primer
<220> FEATURE:
<221> NAME/KEY: misc_feature
<222> LOCATION: (65)..(65)
<223> OTHER INFORMATION: n is a, c, g, or t

<400> SEQUENCE: 17
caagcagaag acggcatacg agattggtca gtgactggag ttcagacgtg tgctcttccg    60
atctntgaca cttgctaata tct                                            83

<210> SEQ ID NO 18
<211> LENGTH: 84
<212> TYPE: DNA
<213> ORGANISM: Artificial Sequence
<220> FEATURE:
<223> OTHER INFORMATION: R5 Primer
<220> FEATURE:
<221> NAME/KEY: misc_feature
<222> LOCATION: (65)..(66)
<223> OTHER INFORMATION: n is a, c, g, or t

<400> SEQUENCE: 18
caagcagaag acggcatacg agatcactgt gtgactggag ttcagacgtg tgctcttccg    60
atctnntgac acttgctaat atct                                           84

<210> SEQ ID NO 19
```

```
<211> LENGTH: 84
<212> TYPE: DNA
<213> ORGANISM: Artificial Sequence
<220> FEATURE:
<223> OTHER INFORMATION: R6 Primer
<220> FEATURE:
<221> NAME/KEY: misc_feature
<222> LOCATION: (65)..(66)
<223> OTHER INFORMATION: n is a, c, g, or t

<400> SEQUENCE: 19
caagcagaag acggcatacg agatattggc gtgactggag ttcagacgtg tgctcttccg        60
atctnntgac acttgctaat atct                                              84

<210> SEQ ID NO 20
<211> LENGTH: 85
<212> TYPE: DNA
<213> ORGANISM: Artificial Sequence
<220> FEATURE:
<223> OTHER INFORMATION: R7 Primer
<220> FEATURE:
<221> NAME/KEY: misc_feature
<222> LOCATION: (65)..(67)
<223> OTHER INFORMATION: n is a, c, g, or t

<400> SEQUENCE: 20
caagcagaag acggcatacg agatgatctg gtgactggag ttcagacgtg tgctcttccg        60
atctnnntga cacttgctaa tatct                                             85

<210> SEQ ID NO 21
<211> LENGTH: 85
<212> TYPE: DNA
<213> ORGANISM: Artificial Sequence
<220> FEATURE:
<223> OTHER INFORMATION: R8 Primer
<220> FEATURE:
<221> NAME/KEY: misc_feature
<222> LOCATION: (65)..(67)
<223> OTHER INFORMATION: n is a, c, g, or t

<400> SEQUENCE: 21
caagcagaag acggcatacg agattcaagt gtgactggag ttcagacgtg tgctcttccg        60
atctnnntga cacttgctaa tatct                                             85

<210> SEQ ID NO 22
<211> LENGTH: 18
<212> TYPE: DNA
<213> ORGANISM: Artificial Sequence
<220> FEATURE:
<223> OTHER INFORMATION: 22. M5-15; QGRS

<400> SEQUENCE: 22
ggtacggcgc ggtggcgg                                                     18

<210> SEQ ID NO 23
<211> LENGTH: 13
<212> TYPE: DNA
<213> ORGANISM: Artificial Sequence
<220> FEATURE:
<223> OTHER INFORMATION: a-syn-1 QGRS

<400> SEQUENCE: 23
ggggtgggta cgg                                                          13

<210> SEQ ID NO 24
<211> LENGTH: 18
```

```
<212> TYPE: DNA
<213> ORGANISM: Artificial Sequence
<220> FEATURE:
<223> OTHER INFORMATION: a-syn-2 QGRS

<400> SEQUENCE: 24
ggtacggcgc ggtggcgg                                                    18

<210> SEQ ID NO 25
<211> LENGTH: 21
<212> TYPE: DNA
<213> ORGANISM: Artificial Sequence
<220> FEATURE:
<223> OTHER INFORMATION: a-syn-3 QGRS

<400> SEQUENCE: 25
ggggtggtga cgtcagcatg g                                                21

<210> SEQ ID NO 26
<211> LENGTH: 19
<212> TYPE: DNA
<213> ORGANISM: Artificial Sequence
<220> FEATURE:
<223> OTHER INFORMATION: a-syn-4 QGRS

<400> SEQUENCE: 26
ggaatggcgc ggtgaccgg                                                   19
```